(12) United States Patent
Gong et al.

(10) Patent No.: US 8,048,912 B2
(45) Date of Patent: Nov. 1, 2011

(54) BENZOPYRAN DERIVATIVES HAVING INHIBITORY ACTIVITIES AGAINST LIVER FIBROSIS AND CIRRHOSIS AND THEIR PHARMACEUTICAL USES

(75) Inventors: Young-Dae Gong, Daejeon (KR); Jin-Soo Seo, Daejeon (KR); Moon-Kook Jeon, Daejeon (KR); Wie-Jong Kwak, Seoul (KR); Yong-Baik Cho, Anyang-si (KR); Nam Kyu Lee, Suwon-si (KR); Eun Ju Lee, Seoul (KR); Jung Bum Lee, Suwon-si (KR); Jun Won Lee, Gunpo-si (KR); Sukho Lee, Suwon-si (KR); Mi-Sook Dong, Seoul (KR); Jeong-Ran Kim, Seoul (KR)

(73) Assignees: SK Chemicals Co., Ltd., Gyeonggi-do (KR); Korea Research Institute of Chemical Technology, Daejeon (KR)

( * ) Notice: Subject to any disclaimer, the term of this patent is extended or adjusted under 35 U.S.C. 154(b) by 859 days.

(21) Appl. No.: 11/794,564

(22) PCT Filed: Jun. 15, 2005

(86) PCT No.: PCT/KR2005/001833
§ 371 (c)(1),
(2), (4) Date: Apr. 2, 2008

(87) PCT Pub. No.: WO2006/070984
PCT Pub. Date: Jul. 6, 2006

(65) Prior Publication Data
US 2009/0118302 A1      May 7, 2009

(30) Foreign Application Priority Data

Dec. 31, 2004 (KR) .................. 10-2004-0117707
Dec. 31, 2004 (KR) .................. 10-2004-0117711

(51) Int. Cl.
*A61K 31/352* (2006.01)
*C07D 311/60* (2006.01)
*C07D 311/70* (2006.01)
(52) U.S. Cl. ................................ 514/456; 549/404
(58) Field of Classification Search ............. 549/404; 514/456
See application file for complete search history.

(56) References Cited

U.S. PATENT DOCUMENTS

| 4,681,890 A | 7/1987 | Kanehira et al. |
| 5,703,075 A | 12/1997 | Gammill et al. |
| 5,763,470 A | 6/1998 | Tang et al. |
| 6,492,390 B2 | 12/2002 | Carter et al. |

*Primary Examiner* — Bernard Dentz
(74) *Attorney, Agent, or Firm* — Frommer Lawrence & Haug LLP; Ronald R. Santucci

(57) ABSTRACT

The present invention relates to a novel benzopyran derivative having goodantagonistic activity on TGF-β receptor which can be effectively used as a prophylactic and therapeutic agent for liver disease as well as several fibroplasiadiseases such as hepatic fibrosis, liver cirrhosis, pulmonary fibrosis, dermatosclerosis, glomerular fibrosis and the like; and a pharmaceutical use thereof.

8 Claims, 6 Drawing Sheets

[Fig. 7]
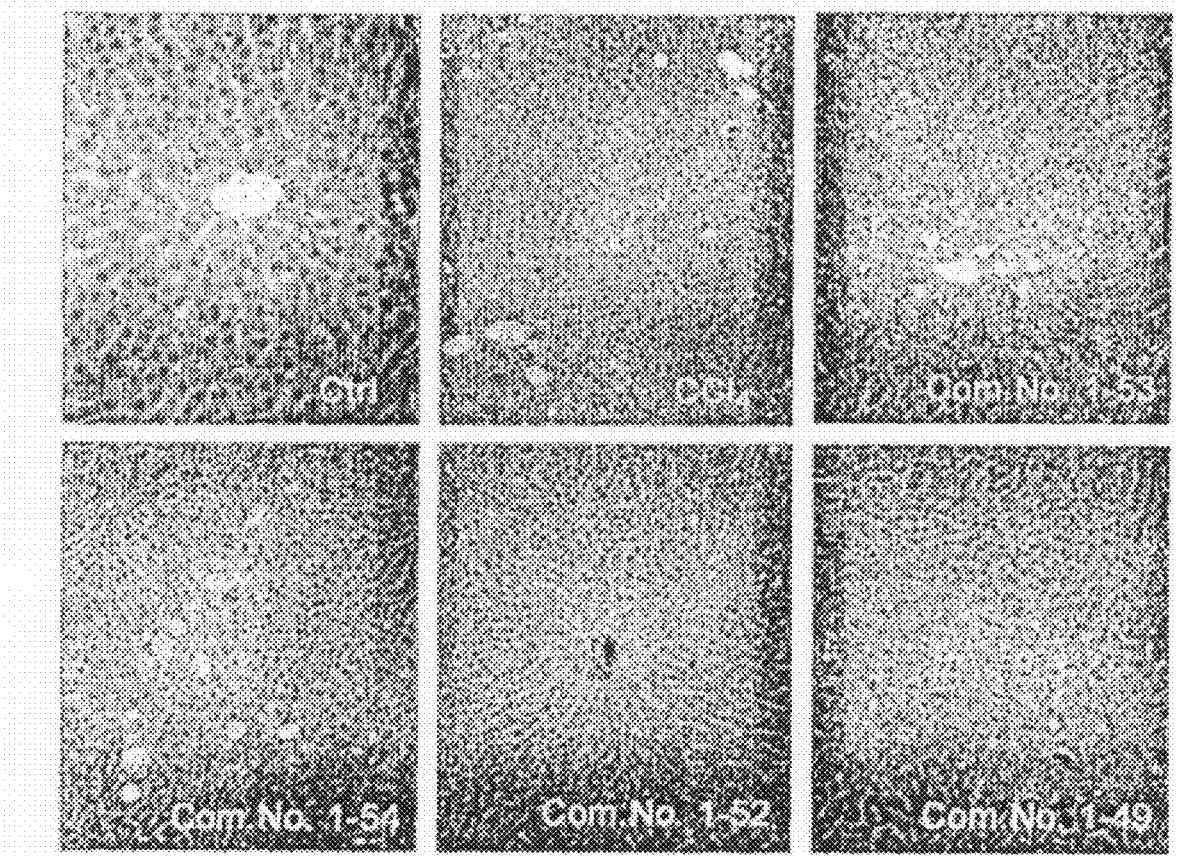

BENZOPYRAN DERIVATIVES HAVING INHIBITORY ACTIVITIES AGAINST LIVER FIBROSIS AND CIRRHOSIS AND THEIR PHARMACEUTICAL USES

This application is a 371 of PCT/KR2005/001833 filed on Jun. 15, 2005, published on Jul. 6, 2006 under publication number WO 2006/070984 A1 which claims priority benefits from Korean Patent Application No. 10-2004-0117711 filed Dec. 31, 2004 and Korean Patent Application No. 10-2004-0117707 filed Dec. 31, 2004, the disclosures of which are hereby incorporated by reference.

FIELD OF THE INVENTION

The present invention relates to a novel benzopyran derivative having good antagonistic activity on TGF-β receptor which can be effectively used both as a prophylactic and a therapeutic agent for treating liver disease as well as several fibroplasia diseases such as hepatic fibrosis, liver cirrhosis, pulmonary fibrosis, dermatosclerosis, glomerular fibrosis and so on; and a pharmaceutical use thereof.

BACKGROUND OF THE INVENTION

Liver plays an important role of metabolizing exogenous and endogenous substances in human body. When liver tissues are continuously exposed to frequent alcoholic drinking or crapulence, viral infection or drug misuse and abuse, the liver tissues are easily damaged and subsequently develop into chronic liver diseases such as hepatic fibrosis and liver cirrhosis. Since hepatic fibrosis does not show any pain or a particular symptom until it is discovered at a terminal stage, its death rate is relatively high and thus its development often becomes a social problem.

In particular, liver disease can be divided into several procedural symptoms. The damaged tissues are first converted into fatty liver in its early stage and then developed into hepatitis, and finally into hepatic fibrosis and liver cirrhosis. Generally, it has been reported that the progress up to hepatic fibrosis is reversible, but once it is developed into liver cirrhosis, its subsequent process becomes irreversible. Accordingly, liver disease can be cured by administering a drug at a stage prior to the development of hepatic fibrosis or an early fibrosis stage.

Liver cirrhosis is caused by fibrosis of liver tissues. Liver fibrosis is a condition that the balance between the synthesis and degradation procedures of a connective tissue is lost, caused by excessive accumulation of connective tissues within liver tissues, and accompanied by necrosis or inflammation. In particular, hepatic stellate cells (HSCs) that store vitamin A in normal liver are converted into myofibroblasts by acute and chronic liver damage, rapidly proliferate and synthesize an excessive amount of connective tissues through the increase in the synthesis and translocation of an extracellular matrix such as collagen, proteoglycan or hyaluronan, which results in stimulating the progression of liver fibrosis [Friedman et al., Proc. Natl. Acad. Sci. USA., 82: 8681 (1985) Gressner et al., Biochem. Biophys. Res. Commun., 151: 222 (1988) Gressner et al., J. Hepatol., 22: 28 (1995)]. In such procedure, TGF-β is synthesized, secreted and activated by several kinds of cells in the liver tissues, in particular, Kupffer cells or hepatic stellate cells activated by TGF-β, induce the proliferation and development of hepatic stellate cells, and thereby, play an important role in inducing the over-production and accumulation of an extracellular matrix such as collagen. It has been reported that in chronic liver disease such as hepatic fibrosis or liver cirrhosis, TGF-β is only expressed in the liver tissues undergoing fibrosis, increases the amount of an extracellular matrix, and finally, stimulates the progression of hepatic fibrosis [Bauer and Schuppan, FEBS Lett. 502:1-3 (2001); Bedossa and Paradis, J Hepatol., 22 (Suppl. 2):37-4 (1995)].

Until now, the development of an inhibitor for hepatic fibrosis or a therapeutic agent for liver cirrhosis has been focused on the development of a drug which inhibits the over-production of a connective tissue (representatively, collagen) of hepatic stellate cells or inhibits the growth thereof, but it has not yet been developed as an effective therapeutic agent. Recently, studies have been actively conducted on the inhibition of TGF-β function or TGF-β receptor activation as a target for developing a new therapeutic agent for liver cirrhosis, based on the fact that TGF-β is the strongest inducible factor for fibrosis of hepatic stellate cells among cytokines involved in fibrosis.

The present inventors have therefore synthesized numerous compounds having antagonistic activity on TGF-β receptor, endeavored to screen a new compound capable of inhibiting or preventing hepatic fibrosis among them by employing hepatic stellate cells that play an important role in the progression of hepatic fibrosis, and finally, found that a benzopyran derivative having a novel structure shows significant prophylactic and therapeutic effect.

DETAILED DESCRIPTION OF THE INVENTION

The present inventors have synthesized various benzopyran derivatives based on the fact that natural and synthetic substances having a benzopyran backbone show a pharmacological efficacy broadly suppressing active oxygen, and studied their antagonistic activities for TGF-β receptor which strongly induces fibrosis of hepatic stellate cells, and the inhibition of collagen synthesis and cell proliferation by using hepatic stellate cells which are known as a major cause of hepatic fibrosis. As a result, it is discovered now that a thiourea- or a guanidine-based benzopyran derivative shows an inhibitory effect on hepatic fibrosis through antagonistic activity on TGF-β receptor and the inhibition of collagen synthesis.

Accordingly, in an embodiment of the present invention, there is provided a novel benzopyran derivative useful for developing a therapeutic agent for liver cirrhosis and a method for its preparation.

In another embodiment of the present invention, there is provided a use of the novel benzopyran derivative as both a prophylactic and a therapeutic agent for liver diseases caused by the activation and over-production of TGF-β and the excessive accumulation of an extracellular matrix such as collagen.

In a further embodiment of the present invention, there is provided a benzopyran derivative described in Formula (1):

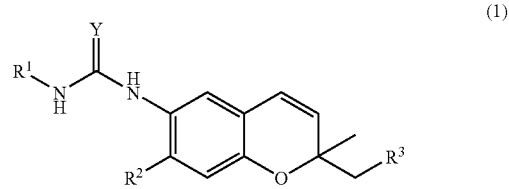

(1)

wherein Y is S or N—R$^4$;

R$^1$ and R$^4$ are independently C$_1$-C$_{20}$ alkyl, amine, substituted or unsubstituted phenyl, substituted or unsubstituted benzyl, dioxobenzyl, isovaline(methylester), naphtyl, or phenyl-X— (wherein X is carbonyl, or C$_1$-C$_6$ alkyl), or R$^1$ and R$^4$ are fused together with the nitrogen atom to which they are attached to form a heterocycle having a 5- to 7-member ring;

R$^2$ is hydrogen, or C$_1$-C$_5$ alkyl;

R$^3$ is hydrogen, C$_1$-C$_5$ alkyl, substituted or unsubstituted phenyl, or substituted or unsubstituted benzyl; and wherein the substituted phenyl or the substituted benzyl is phenyl or benzyl replaced with 1 to 4 substituents selected from the group consisting of halogen, nitro, benzyloxy, C$_1$-C$_5$ alkyl, C$_1$-C$_5$ alkoxy, C$_1$-C$_5$ haloalkyl, C$_1$-C$_5$ alkylsulfide, and C$_1$-C$_5$ alkylsulfanyl.

Further, since in case of presenting a different substituent at the position 2 of benzopyran in the benzopyran derivative of Formula (1) in accordance with the present invention, the benzopyran derivative has an optical activity, isomers of the compound of Formula (1) may be included in the scope of the present invention.

Of the compounds of Formula (1) according to the present invention, the preferred ones are:

those wherein R$^1$ and R$^4$ are independently C$_1$-C$_{20}$ straight, branched and cyclic alkyl; amine; phenyl; phenyl replaced with 1 to 4 substituents selected from the group consisting of halogen, nitro, benzyloxy, C$_1$-C$_5$ alkyl, C$_1$-C$_5$ alkoxy, C$_1$-C$_5$ haloalkyl, C$_1$-C$_5$ alkylsulfide, and C$_1$-C$_5$ alkylsulfanyl; benzyl; benzyl replaced with halogen; dioxobenzyl; isovaline (methylester); morphorino; naphtyl; or R$^1$ and R$^4$ are fused together with the nitrogen atom to which they are attached to form piperidine, piperidine replaced with C$_1$-C$_5$ alkoxycarbonyl, piperazine, or piperazine replaced with phenyl;

R$^2$ is hydrogen, or C$_1$-C$_5$ alkyl; and

R$^3$ is hydrogen, C$_1$-C$_5$ alkyl, phenyl, or benzyl.

In a still further embodiment of the present invention, there is provided a method for preparing the compound of Formula (1) by using a liquid phase high-throughput synthetic technique, which is described in Reaction Scheme 1 as follows:

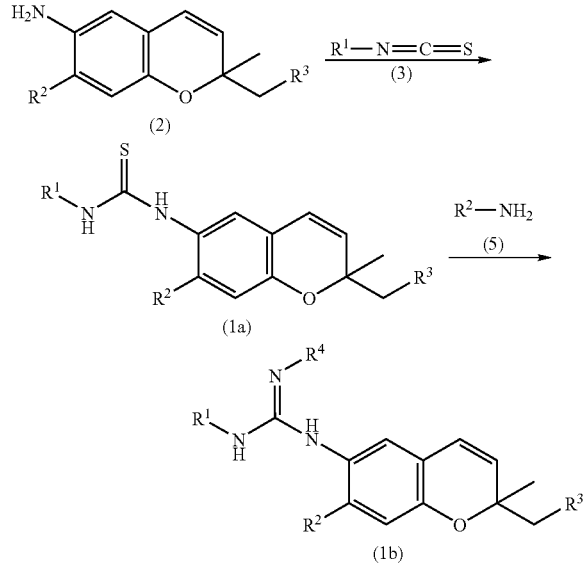

wherein R$^1$, R$^2$, R$^3$, and R$^4$ have the same meanings as defined in Formula (1).

6-Amino-2,7-disubstituted-2-methyl-2H-chromen of Formula (2) used as a starting material in the preparation method of the present invention is a known compound, which can be easily synthesized according to a conventional method in the art.

The preparation method of the present invention in accordance with Reaction Scheme 1 comprises: (1) synthesizing a thiourea-based benzopyran derivative of Formula (1a) by reacting 6-Amino-2,7-disubstituted-2-methyl-2H-chromen of Formula (2) with an isothiocyanate derivative of Formula (3); and (2) synthesizing a guanidine-based benzopyran derivative of Formula (1b) by reacting the thiourea-based benzopyran derivative of Formula (1a) with an amine derivative of Formula (5).

Further, the preparation method of the present invention is characterized by the step of removing the unreacted isothiocyanate of Formula (3) after the step (1) is completed and the unreacted amine derivative of Formula (5) after the step (2) is completed by filtration using a scavenger resin, respectively.

Namely, the method of the present invention can synthesize a large amount of the thiourea-based benzopyran derivative at the same time within a relatively short period of time while removing the unreacted isothiocyanate derivative of Formula (3) after the step (1) is completed by filtration using the scavenger resin having an amine group of Formula (4):

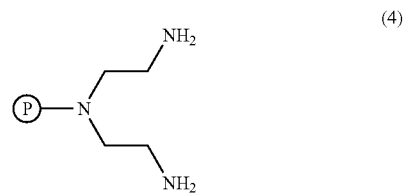

wherein Ⓟ is a solid support in the form of a polymer selected from the group consisting of polystyrene, polystyrene-divinylbenzene, polymethacrylic acid-dimethylacrylamide and polyhydroxy methacrylic acid.

Further, since the method of the present invention can purify a large amount of reactants simultaneously while removing the unreacted amine derivative of Formula (5) after the step (2) is completed by filtration using the scavenger resin containing an isocyanate group of Formula (6), it is capable of synthesizing the guanidine-based benzopyran derivative within a short period:

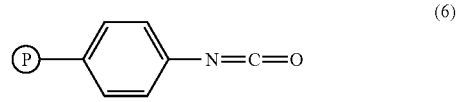

wherein Ⓟ is a solid support in the form of a polymer selected from the group consisting of polystyrene, polystyrene-divinylbenzene, polymethacrylic acid-dimethylacrylamide and polyhydroxy methacrylic acid.

A reaction process, composition of a solvent system and selectable range of a reaction condition in accordance with the present invention are described in more detail as follows. For the purpose of conducting the preparation method of the present invention, it is desirable to use a solvent having a high swelling effect of a resin considering the use of a scavenger resin at a final step. In particular, the solvent employable in the present invention includes dichloromethane (CH$_2$Cl$_2$), chloroform (CHCl$_3$), tetrahydrofuran (THF) and the like. In the above step (1), in order to incorporate R¹ substitutent, it is preferable to use the isocyanate derivative replaced with R¹ of Formula (3) in the amount ranging from 1.2 to 2.0 equivalents, and preferably, the use of 1.2 equivalents is more economical. In the step (2), it is preferable to use the amine derivative replaced with R² of Formula (5) in the amount ranging from 1.2 to 2.0 equivalents based on the amount of thiounrea based benzopyran derivative of Formula (1a), and it is more preferable to use 1.2 equivalents of the amine derivative in terms of cost-effectiveness.

Further, in order to confirm the production of a target compound in the course of carrying out the preparation method of the present invention, the final reactant may be separated and purified by using a high-throughput multiple column chromatography (Quad³⁺; Biotage, USA) and automatic sample injector at a final step, and then, subjected to a structural analysis with NMR and Mass spectra.

Furthermore, since 6-Amino-2,7-disubstituted-2-methyl-2H-chromen of Formula (2) used as a starting material and a target product, banzopyran derivatives of Formula (1) in the preparation method according to the present invention have their optical isomers, respectively, each of their pure optical isomer compounds may be separated by means of a conventional purification method well-known in the art upon necessity.

Meanwhile, the compound of the present invention can be used as an effective prophylactic and therapeutic agent for treating various liver diseases caused by TGF-β activity, collagen synthesis activity, and liver cirrhosis activity. Accordingly, the present invention includes a prophylactic as well as a therapeutic agent for treating liver diseases comprising the benzopyran derivative of Formula (1) or a pharmaceutically acceptable salt thereof as an active ingredient. Further, since the compound in accordance with the present invention has high antagonistic activity on TGF-β receptor, it can be also used for preventing and treating various fibroplasia diseases such as hepatic fibrosis, liver cirrhosis, pulmonary fibrosis, dermatosclerosis, glomerular fibrosis and the like.

The pharmaceutically acceptable salt in the present invention can be prepared according to a conventional method well-known in the art, e.g., by reacting the compound of the present invention with an inorganic acid such as hydrochloric acid, hydrobromide, sulfuric acid, sodium hydrogen sulfate, phosphoric acid or carbonic acid; an organic acid such as formic acid, acetic acid, oxalic acid, benzoic acid, citric acid, tartaric acid, gluconic acid, gestisic acid, fumaric acid, lactobionic acid, salicylic acid, or acetylsalicylic acid (aspirin); an alkali metal ion such as sodium or potassium; or ammonium ion.

Further, the pharmaceutical composition of the present invention may further comprise a conventionally atoxic, pharmaceutically acceptable carrier, adjuvant and excipient in addition to the benzopyran derivative or the pharmaceutically acceptable salt thereof, and be formulated into a conventional formulation in a pharmaceutical field, e.g., a formulation for oral administration such as tablets, capsules, troches, liquids or emulsions, or a formulation for parental administration. Further, for treating a human patient, a typical daily dose of the inventive compound as an active ingredient may range from about 0.01 to 1000 mg/day based on an adult patient having 70 kg of body weight, and can be administered in a single dose or in divided doses. However, it should be understood that the amount of the active ingredient actually administered ought to be determined in light of various relevant factors including the condition to be treated, the chosen route of administration, the age, sex and body weight of the individual patient, and the severity of the patient's symptom; and, therefore, the above dose should not be intended to limit the scope of the invention in any way.

BRIEF DESCRIPTION OF THE DRAWINGS

FIG. 7 is a result of an animal experiment (in vivo) showing the effect of N-(2,7-di substituted-2-methyl-2H-chromen-6-yl)thiourea derivative on the inhibition and treatment of hepatic fibrosis/liver cirrhosis.

Figure 1:
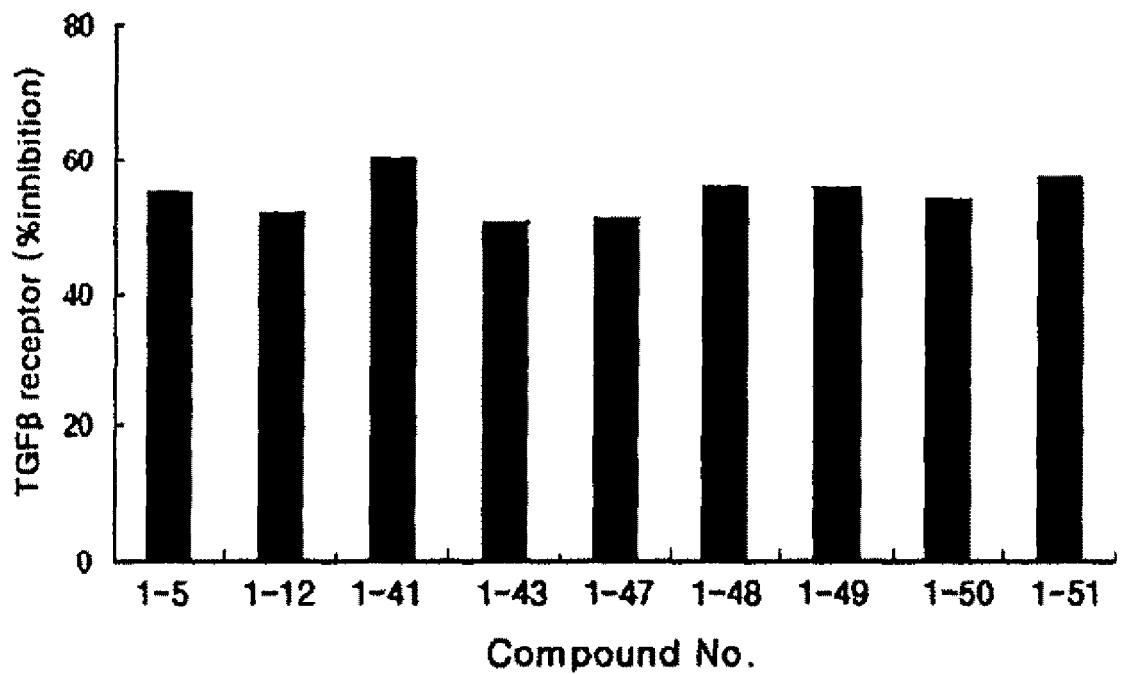
FIG. 1 is a graph showing antagonistic activity on TGF-β receptor of N-(2,7-di substituted-2-methyl-2H-chromen-6-yl)thiourea derivative.
Figure 1:
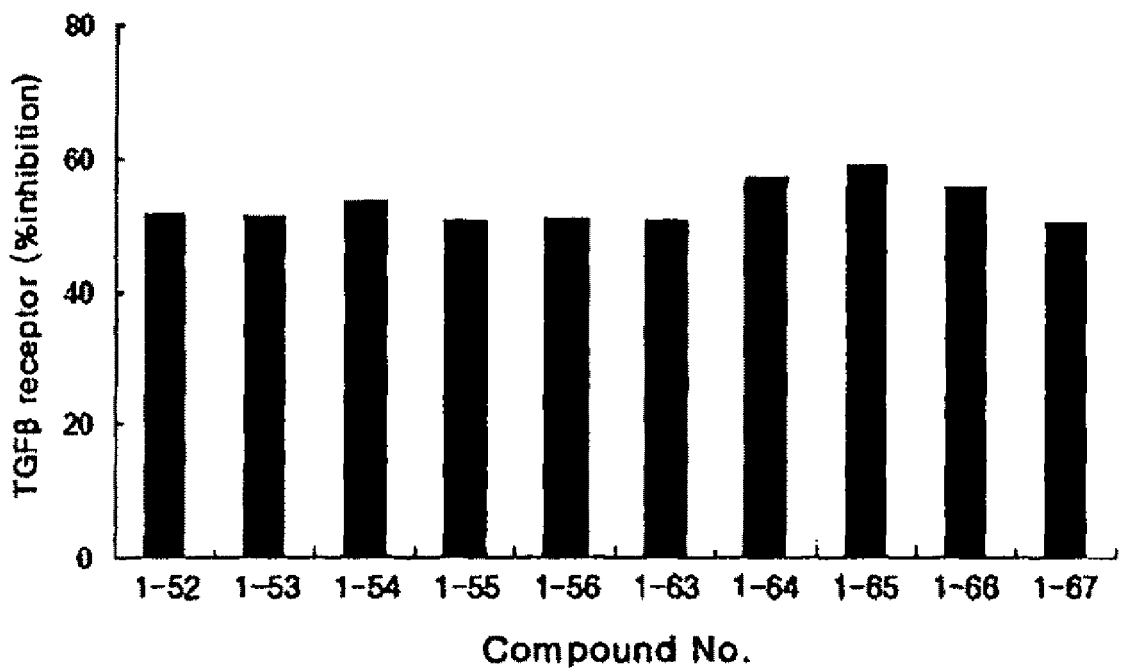

The present invention is further illustrated in the following Examples. It should be understood that these Examples, while indicating preferred embodiments of the invention, are given by way of illustration only.

BEST MODE

Example 1

Synthesis of Thiourea-Based Benzopyran Derivative Formula 1a

Example 1-1

Synthesis of 1-(2,2'-dimethyl-2H-chromen-6-yl)-3-phenyl-thiourea

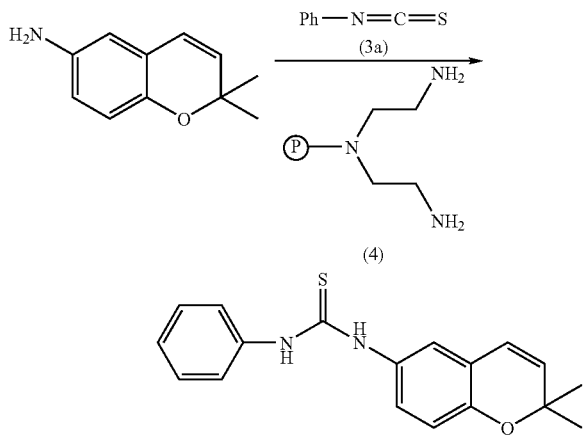

After a benzopyrene compound (100.0 mg, 0.57 mmol) was dissolved in dichloromethane (DCM, 2 mL) and stirred at room temperature for 10 min, phenyl isothiocyanate of Formula (3a) (C$_6$H$_4$NCS; 92.0 mg, 0.68 mmol, 1.2 eq) was added thereto, and the mixture was stirred at the same temperature for 15 hrs. After the reaction was completed, polystyrene diamine of Formula (4) (3.0 mmol/g, 0.34 g, 1 mmol) was added to the reactant and stirred for 30 min. The reactant was subjected to filtration to separate a filtrate. The filtrate was repeatedly washed with chloroform (CHCl$_3$) and collected. The resulting reactant was concentrated under reduced pressure and the residue thus obtained was purified with a silica gel column chromatography using a mixed solvent of hexane/ethylacetate (4/1, v/v), to obtain the title compound (115 mg) with a yield of 65%.

$^1$H NMR (300 MHz, CDCl$_3$) δ 8.23 (d, 1H, J=7.9 Hz), 7.77 (s, 1H), 7.39 (s, 1H), 7.38-7.27 (m, 2H), 7.14-7.08 (m, 3H), 7.00 (d, 2H), 6.82 (d, 1H, J=8.5 Hz), 6.30 (d, 1H, J=9.9 Hz), 5.69 (d, 1H, J=9.9 Hz), 1.45 (s, 6H); m/z 310.42

Example 1-2

Synthesis of 1-(2,2'-dimethyl-2H-chromen-6-yl)-3-(4-nitrophenyl)-thiourea

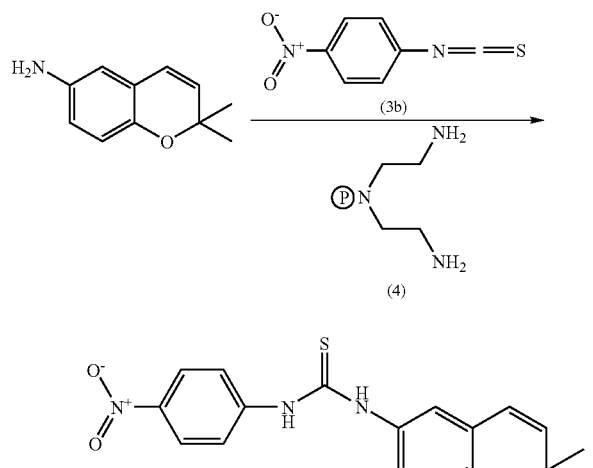

After a benzopyrene compound (100.0 mg, 0.57 mmol) was dissolved in dichloromethane (DCM, 15 mL) and stirred at room temperature for 10 min, 4-nitrophenyl isothiocyanate of Formula (3b) (4-O$_2$NC$_6$H$_4$NCS; 122 mg, 0.68 mmol, 1.2 eq) was added thereto, and the mixture was stirred at the same temperature for 15 hrs. After the reaction was completed, polystyrene diamine of Formula (4) (3.0 mmol/g, 0.34 g, 1 mmol) was added to the reactant and stirred for 30 min. The reactant was subjected to filtration to separate a filtrate. The filtrate was repeatedly washed with chloroform (CHCl$_3$) and collected. The resulting reactant was concentrated under reduced pressure and the residue thus obtained was purified with a silica gel column chromatography using a mixed solvent of hexane/ethylacetate (4/1, v/v), to obtain the title compound (150 mg) with a yield of 74%.

$^1$H NMR (200 MHz, CDCl$_3$) δ 8.20 (d, 2H, J=9.2 Hz), 7.75 (d, 2H, J=9.2 Hz), 7.07 (m, 1H), 6.94-6.83 (m, 2H), 6.30 (d, 1H, J=9.8 Hz), 5.72 (d, 1H, F=9.8 Hz), 1.47 (s, 6H); m/z 355.44

Example 1-3

Synthesis of 1-(2,7-dimethyl-2-propyl-2H-chromen-6-yl)-3-(4-nitrophenyl)-thiourea

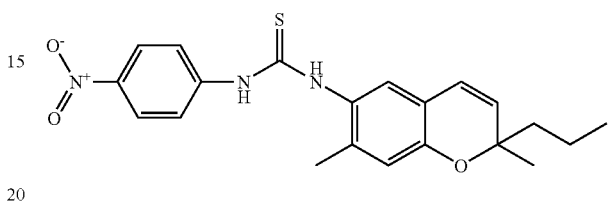

The title compound was obtained according to the same method as described in Example 1-1.

m/z 397.49

Example 1-4

Synthesis of 1-(2-methyl-2-phenethyl-2H-chromen-6-yl)-3-(4-nitrophenyl)-thiourea

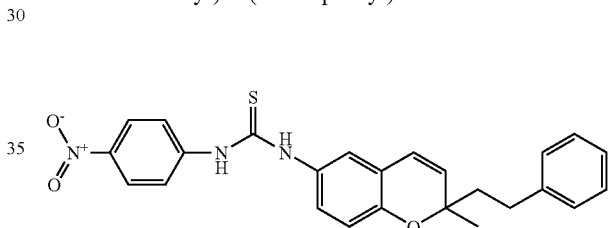

The title compound was obtained according to the same method as described in Example 1-1.

m/z 445.54

Example 1-5

Synthesis of 1-(2,7-dimethyl-2-phenethyl-2H-chromen-6-yl)-3-(4-nitrophenyl)-thiourea

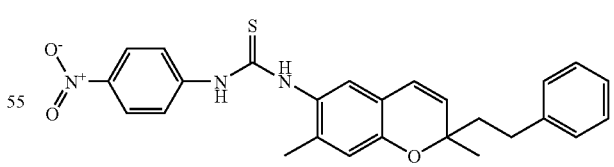

The title compound was obtained according to the same method as described in Example 1-1.

m/z 459.59

Further, the thiourea-based benzopyran derivative of Formula (1a), as a target compound of the present invention, was synthesized according to the same method as described in Example 1, and the results are shown in the following Tables 1a to 1g.

TABLE 1a (1a)

[Structure: thiourea R¹-NH-C(=S)-NH- attached to a 2H-chromene bearing R² at position 7, methyl and CH₂R³ at position 2, thiourea at position 6]

| Com. No. | R¹ | R² | R³ | Structural data |
|---|---|---|---|---|
| 1-1 | Ph | H | H | ¹H NMR(300 MHz, CDCl₃): δ 8.23(d, 1 H, J = 7.9 Hz), 7.77(s, 1 H), 7.39(s, 1 H), 7.38-7.27(m, 2 H), 7.14-7.08(m, 3 H), 7.00(d, 2 H), 6.82(d, 1 H, J = 8.5 Hz), 6.30(d, 1 H, J = 9.9 Hz), 5.69(d, 1 H, J = 9.9 Hz), 1.45(s, 6 H); m/z 310.42 |
| 1-2 | 4-O₂N-Ph | H | H | ¹H NMR(200 MHz, CDCl₃): δ 8.20(d, 2 H, J = 9.2 Hz), 7.75(d, 2 H, J = 9.2 Hz), 7.07(m, 1 H), 6.94-6.83(m, 2 H), 6.30(d, 1 H, J = 9.8 Hz), 5.72(d, 1 H, J = 9.8 Hz), 1.47(s, 6 H); m/z 355.44 |
| 1-3 | 3,4-di-Cl-Ph | H | H | ¹H NMR(300 MHz, CDCl₃): δ 7.73(br, 1 H), 7.59-7.58(m, 1 H), 7.43-7.40(m, 1 H), 7.36-7.32(m, 1 H), 7.06-7.02(m, 1 H), 6.93-6.92(m, 1 H), 6.85-6.82(m, 1 H), 6.28(d, 1 H, J = 9.9 Hz), 5.69(d, 1 H, J = 9.9 Hz) |
| 1-4 | 2,4-di-F-Ph | H | H | ¹H NMR(300 MHz, CDCl₃): δ 8.26(br, 1 H), 7.85-7.80(m, 1 H), 7.38(br, 1 H), 7.08-7.05(m, 1 H), 6.96-6.95(m, 1 H), 6.93-6.81(m, 2 H), 6.28(d, 1 H, J = 9.9 Hz), 5.68(d, 1 H, J = 9.9 Hz), 1.45 (s, 6 H) |
| 1-5 | adamantyl | H | H | ¹H NMR(300 MHz, CDCl₃): δ 7.26-7.23(m, 1 H), 6.94-6.91(m, 1 H), 6.81-6.76(m, 2 H), 6.28(d, 1 H, J = 9.9 Hz), 5.70(d, 1 H, J = 9.9 Hz), 2.18(br, 6 H), 2.09(br, 2 H), 1.67(br, 6 H), 1.60(s, 1 H), 1.44(s, 6 H) |
| 1-6 | 2-ethyl-Ph | H | H | ¹H NMR(300 MHz, CDCl₃): δ 7.65(br, 1 H), 7.41-7.38(m, 1 H), 7.30-7.23(m, 4 H), 7.08-7.04(m, 1 H), 6.99-6.98(m, 1 H), 6.78-6.76(m, 1 H), 6.26(d, 1 H, J = 9.8 Hz), 5.63(d, 1 H, J = 9.8 Hz), 2.64(q, 2 H), 1.42(s, 6 H), 1.19(t, 3 H) |

TABLE 1b

| Com. No. | R¹ | R² | R³ | Structural data |
|---|---|---|---|---|
| 1-7 | 2,2,4-Trimethyl-pentyl | H | H | ¹H NMR(300 MHz, CDCl₃): δ 7.22(br, 1 H), 6.94-6.90(m, 1 H), 6.80-6.78(m, 2 H), 6.27(d, 1 H, J = 9.9 Hz), 5.84(br, 1 H), 5.68(d, 1 H, J = 9.9 Hz), 1.54(s, 6 H), 1.44(s, 1 H), 0.91(s, 11 H) |
| 1-8 | 4-(benzyloxy)phenyl | H | H | ¹H NMR(300 MHz, CDCl₃): δ 7.59(br, 2 H), 7.43-7.29(m, 7 H), 7.07-6.97(m, 4 H), 6.78(d, 1 H, J = 8.4 Hz), 6.27(d, 1 H, J = 9.9 Hz), 5.64(d, 1 H, J = 9.9 Hz), 5.08(s, 2 H), 1.43(s, 6 H) |
| 1-9 | Phenethyl | H | H | ¹H NMR(300 MHz, CDCl₃): δ 7.74(br, 1 H), 7.27-7.20(m, 3 H), 7.14-7.11(m, 2 H), 6.74-6.63(m, 3 H), 6.17(d, 1 H, J = 9.9 Hz), 5.81(br, 1 H), 5.66(d, 1 H, J = 9.9 Hz), 3.86(t, 2 H), 2.90(t, 2 H), 1.43(s, 6 H) |
| 1-10 | benzoyl | H | H | ¹H NMR(300 MHz, CDCl₃): δ 12.40(br, 1 H), 9.08(br, 1 H), 7.88(d, 2 H, J = 7.5 Hz), 7.87-7.51(m, 3 H), 7.38-7.35(m, 2 H), 6.80(d, 1 H, J = 9.0 Hz), 6.32(d, 1 H, J = 9.9 Hz), 5.65(d, 1 H, J = 9.9 Hz), 1.44(s, 6 H) |
| 1-11 | cyclohexyl | H | H | ¹H NMR(200 MHz, CDCl₃): δ 7.61(br, 1 H), 6.90(m, 1 H), 6.79-6.74(m, 2 H), 6.25(d, 1 H, J = 10.0 Hz), 5.67(d, 1 H, J = 10.0 Hz), 4.27-4.15(m, 1 H), 2.01(br, 2 H), 1.62(br, 3 H), 1.43(s, 6 H), 1.35(br, 2 H), 1.09(br, 3 H) |
| 1-12 | 2,5-di-MeO-Ph | H | H | ¹H NMR(200 MHz, CDCl₃): δ 8.19(br, 2 H), 7.79(br, 1 H), 7.09-7.03(m, 1 H), 6.98-6.97(m, 1 H), 6.84-6.75(m, 2 H), 6.67-6.61(m, 1 H), 6.25(d, 1 H, J = 10.0 Hz), 5.67(d, 1 H, J = 10.0 Hz), 3.79(s, 3 H), 3.69(s, 3 H), 1.45(s, 6 H) |

TABLE 1b-continued

| | | | | |
|---|---|---|---|---|
| 1-13 | 1-naphthyl | H | H | $^1$H NMR(300 MHz, CDCl$_3$): δ 7.98(br, 1 H), 7.93-7.86(m, 3 H), 7.60-7.50(m, 4 H), 7.07-6.97(m, 2 H), 6.75(d, 1 H, J = 8.4 Hz), 6.26(d, 1 H, J = 9.6 Hz), 5.63(d, 1 H, J = 9.6 Hz), 1.41(s, 6 H) |
| 1-14 | 3-Cl-4-Me-Ph | H | H | $^1$H NMR(200 MHz, CDCl$_3$): δ 7.89(br, 1 H), 7.59(br, 1 H), 7.39(s, 1 H), 7.22(s, 2 H), 7.07-7.02(m, 1 H), 6.95-6.94(m, 1 H), 6.82-6.78(m, 1 H), 6.28(d, 1 H, J = 9.8 Hz), 5.67(d, 1 H, J = 9.8 Hz), 2.34(s, 3 H), 1.44(s, 6 H) |
| 1-15 | 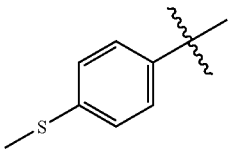 | H | H | $^1$H NMR(300 MHz, CDCl$_3$): δ 7.85(br, 1 H), 7.67(br, 1 H), 7.30(d, 2 H, J = 8.61 Hz), 7.30(d, 2 H, J = 8.61 Hz), 7.25-7.23(d, 2 H, J = 8.61 Hz), 7.07 7.04(m, 1 H), 6.96-6.95(m, 1 H), 6.79(d, 1 H, J = 8.4 Hz), 6.27(d, 1 H, J = 9.9 Hz), 5.65(d, 1 H, J = 9.9 Hz), 2.47(s, 3 H), 1.44(s, 6 H) |

TABLE 1c

| | | | | |
|---|---|---|---|---|
| 1-16 | 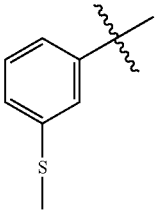 | H | H | $^1$H NMR(200 MHz, CDCl$_3$): δ 7.79(br, 1 H), 7.66(br, 1 H), 7.31(s, 1 H), 7.30-7.23(m, 1 H), 7.15-7.02(m, 3 H), 6.96-6.95(m, 1 H), 6.78(d, 1 H, J = 8.5 Hz), 6.27(d, 1 H, J = 10.0 Hz), 5.66(d, 1 H, J = 10.0 Hz), 2.47(s, 3 H), 1.44 (s, 6 H) |
| 1-17 | 2-isopropyl-Ph | H | H | $^1$H NMR(300 MHz, CDCl$_3$): δ 7.65(br, 1 H), 7.38 7.22(m, 4 H), 7.07-6.98(m, 1 H), 6.76(d, 1 H, J = 8.5 Hz), 6.26(d, 1 H, J = 9.8 Hz), 5.63(d, 1 H, J = 9.8 Hz), 3.17-3.13(m, 1 H), 1.42(s, 6 H), 1.24(s, 6 H) |
| 1-18 | 5-Cl-2-MeO-Ph | H | H | $^1$H NMR(200 MHz, CDCl$_3$): δ 7.09-6.95(m, 3 H), 6.85-6.73(m, 3 H), 6.31(d, 1 H, J = 9.8 Hz), 5.69(m, 1 H, J = 9.8 Hz), 3.73(s, 3 H), 1.46(s, 6 H) |
| 1-19 | 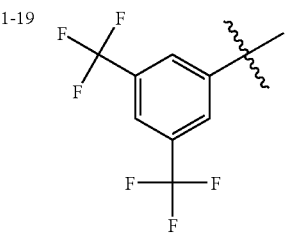 | H | H | $^1$H NMR(300 MHz, CDCl$_3$): δ 8.41(br, 1 H), 7.98(s, 2 H), 7.67(s, 2 H), 7.07-7.03(m, 1 H), 6.93-6.92(m, 1 H), 6.84(d, 1 H, J = 8.5 Hz), 6.28(d, 1 H, J = 9.9 Hz), 5.71(d, 1 H, J = 9.9 Hz), 1.46(s, 6 H) |
| 1-20 | 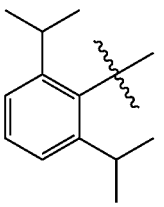 | H | H | $^1$H NMR(200 MHz, CDCl$_3$): δ 8.02(br, 1 H), 7.28-7.24(m, 3 H), 6.89-6.67(m, 3 H), 6.23(d, 1 H, J = 9.8 Hz), 5.58(d, 1 H, J = 9.8 Hz), 3.36-3.22(m, 2 H), 1.44-1.09(m, 18 H) |
| 1-21 | 3,5-di-Me-Ph | H | H | $^1$H NMR(200 MHz, CDCl$_3$): δ 7.82(br, 2 H), 7.08 6.89(m, 5 H), 6.75(d, 1 H, J = 8.5 Hz), 6.27(d, 1 H, J = 9.6 Hz), 5.64(d, 1 H, J = 9.6 Hz), 2.30(s, 6 H), 1.42(s, 6 H) |
| 1-22 | 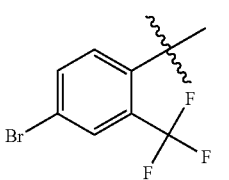 | H | H | $^1$H NMR(200 MHz, CDCl$_3$): δ 8.30(br, 1 H), 7.89(d, 1 H, J = 8.5 Hz), 7.73-7.64(m, 2 H), 7.48(br, 1 H), 7.07-7.02(m, 1 H), 6.95-6.93(m, 1 H), 6.82(d, 1 H, J = 8.3 Hz), 6.29(d, 1 H, J = 9.8 Hz), 5.68(d, 1 H, J = 9.8 Hz), 1.43(s, 6 H) |

TABLE 1c-continued

| | | | | |
|---|---|---|---|---|
| 1-23 | 2-F-Ph | H | H | ¹H NMR(200 MHz, CDCl₃): δ 8.06-8.01(m, 1 H), 7.98(br, 1 H), 7.53(br, 1 H), 7.22-7.04(m, 4 H), 6.98-6.96(m, 1 H), 6.82(d, 1 H, J = 8.5 Hz), 6.29(d, 1 H, J = 9.8 Hz), 5.68(d, 1 H, J = 9.8 Hz), 1.45(s, 6 H) |
| 1-24 | 3-Me-Ph | H | H | ¹H NMR(200 MHz, CDCl₃): δ 7.80(br, 2 H), 7.27-7.16(m, 4 H), 7.09-7.04(m, 1 H), 6.98-6.97(m, 1 H), 6.77(d, 1 H, J = 8.3 Hz), 6.28(d, 1 H, J = 9.8 Hz), 5.65(d, 1 H, J = 9.8 Hz), 2.35(s, 3 H), 1.43(s, 6 H) |
| 1-25 | 3-MeO-Ph | H | H | ¹H NMR(300 MHz, CDCl₃): δ 7.58(br, 2 H), 7.30-7.24(m, 2 H), 7.09-6.89(m, 4 H), 6.78(d, 1 H, J = 8.5 Hz), 6.28(d, 1 H, J = 9.8 Hz), 5.65(d, 1 H, J = 9.8 Hz), 3.81(s, 3 H), 1.44(s, 6 H) |

TABLE 1d

| | | | | |
|---|---|---|---|---|
| 1-26 | Cyclopentyl | H | H | ¹H NMR(200 MHz, CDCl₃): δ 7.62(br, 1 H), 6.95 .81(m, 1 H), 6.80-6.76(m, 2 H), 6.27(d, 1 H, J = 10.0 Hz), 5.67(d, 1 H, J = 10.0 Hz), 4.70-4.59(m, 1 H), 2.12-1.99(br, 2 H), 1.67-1.55(br, 4 H), 1.44(s, 1 H), 1.40 1.25(br, 2 H) |
| 1-27 | 2-(3-F-Ph)propan-2-yl | H | H | ¹H NMR(300 MHz, CDCl₃): δ 7.84(br, 1 H), 7.27 7.23(m, 2 H), 7.03-6.89(m, 3 H), 6.78-6.75(m, 2 H), 6.23(d, 1 H, J = 9.6 Hz), 6.01(br, 1 H), 5.66(d, 1 H, J = 9.6 Hz), 1.44(s, 12 H) |
| 1-28 | Undecyl | H | H | ¹H NMR(200 MHz, CDCl₃): δ 7.66(br, 1 H), 6.97-6.91(m, 1 H), 6.83-6.77(m, 2 H), 6.26(d, 1 H, J = 9.8 Hz), 5.68(d, 1 H, J = 9.8 Hz), 3.64-3.54(m, 2 H), 1.45(s, 6 H), 1.25(s, 9 H), 0.88(t, 3 H) |
| 1-29 | 4-Cl-3-CF₃-Ph | H | H | ¹H NMR(200 MHz, CDCl₃): δ 8.03(br, 1 H), 8.03(br, 1 H), 7.73-7.68(m, 1 H), 7.52-7.45(m, 2 H), 7.09-7.03(m, 1 H), 6.94-6.93(m, 1 H), 6.85(d, 1 H, J = 8.5 Hz), 6.30(d, 1 H, J = 10.0 Hz), 5.71(d, 1 H, J = 10.0 Hz), 1.47(s, 6 H) |
| 1-30 | Heptyl | H | H | ¹H NMR(200 MHz, CDCl₃): δ 7.69(br, 1 H), 6.97-6.91(m, 1 H), 6.83-6.77(m, 2 H), 6.26(d, 1 H, J = 10.0 Hz), 5.82(br, 1 H), 5.68(d, 1 H, J = 10.0 Hz), 3.64-3.54(m, 2 H), 1.45(s, 6 H), 1.26(s, 9 H), 0.87(t, 3 H) |
| 1-31 | 3-CF₃-Ph | H | H | ¹H NMR(200 MHz, CDCl₃): δ 8.31(br, 1 H), 7.72-7.65(m, 2 H), 7.47-7.44(m, 2 H), 7.08-7.02(m, 1 H), 6.94-6.93(m, 1 H), 6.81(d, 1 H, J = 8.5 Hz), 6.28(d, 1 H, J = 9.8 Hz), 1.45(d, 1 H, J = 9.8 Hz), 1.45(s, 6 H) |
| 1-32 | 2-MeO-Ph | H | H | ¹H NMR(200 MHz, CDCl₃): δ 8.02(br, 1 H), 7.83(br, 1 H), 7.18-6.94(m, 4 H), 6.89-6.79(m, 3 H), 6.29(d, 1 H, J = 9.8 Hz), 5.67(d, 1 H, J = 9.8 Hz), 3.76(s, 3 H), 1.45(s, 6 H) |
| 1-33 | 5-Cl-2-Me-Ph | H | H | ¹H NMR(200 MHz, CDCl₃): δ 7.93(br, 1 H), 7.46(s, 1 H), 7.17-7.13(m, 2 H), 7.9-7.03(m, 1 H), 6.97-6.95(m, 1 H), 6.79(d, 1 H, J = 8.5 Hz), 6.28(d, 1 H, J = 10.0 Hz), 5.67(d, 1 H, J = 10.0 Hz), 2.22(s, 3 H), 1.44(s, 6 H) |

TABLE 1d-continued

| | | | | |
|---|---|---|---|---|
| 1-34 | 4-MeO-Ph | H | H | $^1$H NMR(300 MHz, CDCl$_3$): δ 7.69(br, 2 H), 7.27(d, 2 H, J = 9.0 Hz), 7.08-7.04(m, 1 H), 6.98-6.97(m, 1 H), 6.91(d, 2 H, J = 9.0 Hz), 6.77(d, 1 H, J = 8.4 Hz), 6.27(d, 1 H, J = 9.9 Hz), 5.63(d, 1 H, J = 9.9 Hz), 3.80(s, 3 H), 1.43(s, 6 H) |

TABLE 1e

| | | | | |
|---|---|---|---|---|
| 1-35 | Octyl | H | H | $^1$H NMR(300 MHz, CDCl$_3$): δ 7.70(br, 1 H), 6.97-6.91(m, 1 H), 6.83-6.77(m, 2 H), 6.26(d, 1 H, J = 9.8 Hz), 5.83(br, 1 H), 5.68(d, 1 H, J = 9.8 Hz), 3.64-3.54(m, 2 H), 1.71 1.51(m, 2 H), 1.45(s, 6 H), 1.25(s, 10 H), 0.87(t, 3 H) |
| 1-36 | 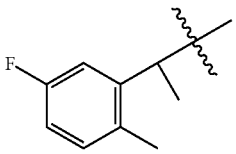 | H | H | $^1$H NMR(300 MHz, CDCl$_3$): δ 7.84(br, 1 H), 7.27-7.23(m, 2 H), 7.03-6.89(m, 3 H), 6.78-6.75(m, 2 H), 6.23(d, 1 H, J = 9.6 Hz), 6.01(br, 1 H), 5.66(d, 1 H, J = 9.6 Hz), 1.44(s, 12 H) |
| 1-37 | 2-Cl-Ph | H | H | $^1$H NMR(300 MHz, CDCl$_3$): δ 7.93(br, 1 H), 7.83(br, 1 H), 7.39-7.27(m, 4 H), 7.08-7.04(m, 1 H), 6.98-6.97(m, 1 H), 6.77(d, 1 H, J = 8.5 Hz), 6.27(d, 1 H, J = 9.8 Hz), 5.65(d, 1 H, J = 9.8 Hz), 1.44(s, 6 H) |
| 1-38 | 2,6-di-Me-Ph | H | H | $^1$H NMR(300 MHz, CDCl$_3$): δ 7.17-6.99(m, 6 H), 6.27(d, 1 H, J = 9.0 Hz), 5.61(d, 1 H, J = 9.0 Hz), 2.35(s, 6 H), 1.43(s, 6 H) |
| 1-39 | 3,5-di-methoxy-Ph | H | H | $^1$H NMR(200 MHz, CDCl$_3$): δ 6.78(br, 1 H), 6.70(s, 1 H), 6.58(s, 1 H), 6.23(d, 1 H, J = 10.0 Hz), 5.49(d, 1 H, J = 10.0 Hz), 3.75-3.73(br, 4 H), 2.15(s, 3 H), 1.69-1.56(br, 6 H), 1.52-1.36(m, 2 H), 1.34(s, 6 H), 0.89(t, 3 H, J = 7.1 Hz) |
| 1-40 | 3,5-di-Me-Ph | Me | H | $^1$H NMR(200 MHz, CDCl$_3$): δ 7.54(br, 1 H), 6.98-6.88(m, 4 H), 6.69(s, 1 H), 6.25(d, 1 H, J = 10.0 Hz), 5.59(d, 1 H, J = 10.0 Hz), 2.31(s, 6 H), 2.30(s, 3 H), 1.43(s, 6 H) |
| 1-41 | Cyclopentyl | Me | H | $^1$H NMR(200 MHz, CDCl$_3$): δ 7.31(br, 1 H), 6.78(s, 1 H), 6.69(s, 1 H), 6.25(d, 1 H, J = 9.8 Hz), 5.63(d, 1 H, J = 9.8 Hz), 5.48-5.45(m, 1 H), 4.71-4.61(m, 1 H), 2.17(s, 3 H), 2.14-1.99(br, 2 H), 1.61-1.49(br, 4 H), 1.44(s, 6 H), 1.39-1.25(br, 2 H) |
| 1-42 | heptyl | Me | H | $^1$H NMR(200 MHz, CDCl$_3$): δ 7.40(br, 1 H), 6.79(s, 1 H), 6.70(s, 1 H), 6.25(d, 1 H, J = 10.0 Hz), 5.63(d, 1 H, J = 10.0 Hz), 3.63-3.53(m, 2 H), 2.18(s, 3 H), 1.71 1.48(m, 2 H), 1.44(s, 6 H), 1.24(s, 8 H), 0.87(t, 3 H) |
| 1-43 | 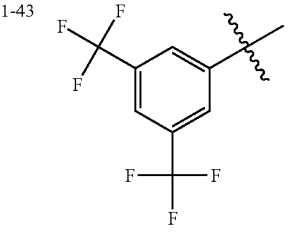 | Me | H | $^1$H NMR(200 MHz, CDCl$_3$): δ 7.93(br, 1 H), 6.94(s, 1 H), 6.75(s, 1 H), 6.54(br, 1 H), 6.28(d, 1 H, J = 9.8 Hz), 5.65(d, 1 H, J = 9.8 Hz), 2.30(s, 3 H), 1.45(s, 6 H) |
| 1-44 | benzoyl | Me | H | $^1$H NMR(200 MHz, CDCl$_3$): δ 9.20(br, 1 H), 7.93 7.88(m, 2 H), 7.66-7.50(m, 3 H), 7.32(s, 1 H), 6.70(s, 1 H), 6.30(d, 1 H, J = 9.8 Hz), 5.59(d, 1 H, J = 9.8 Hz), 2.28(s, 3 H), 1.44(s, 6 H) |

TABLE 1f

| | | | | |
|---|---|---|---|---|
| 1-45 | undecyl | | Me H | $^1$H NMR(200 MHz, CDCl$_3$): δ 7.25(br, 1 H), 6.78(s, 1 H), 6.70(s, 1 H), 6.24(d, 1 H, J = 9.8 Hz), 5.62(d, 1 H, J = 9.8 Hz), 3.63-3.53(m, 2 H), 2.17(s, 3 H), 1.43(s, 6 H), 1.23(s, 8 H), 0.87(t, 3 H) |
| 1-46 | 2-Cl-Ph | | Me H | $^1$H NMR(200 MHz, CDCl$_3$): δ 8.17(br, 1 H), 7.98-7.97(m, 2 H), 7.66(s, 1 H), 7.42(br, 1 H), 6.90(s, 1 H), 6.75(s, 1 H), 6.28(d, 1 H, J = 9.8 Hz), 5.65(d, 1 H, J = 9.8 Hz), 2.28(s, 3 H), 1.45(s, 6 H) |

TABLE 1f-continued

| No. | R | R' | R'' | Data |
|---|---|---|---|---|
| 1-47 | 2-Cl-Ph | Me | H | m/z 358.9 |
| 1-48 | 3-Cl-4-Me-Ph | Me | H | m/z 372.9 |
| 1-49 | 2,6-di-Me-Ph | Me | H | m/z 352.5 |
| 1-50 | 2-ethyl-Ph | Me | H | m/z 352.5 |
| 1-51 | 3-methyl sulfanyl-Ph | Me | H | m/z 370.5 |
| 1-52 | 2-MeO-Ph | Me | H | m/z 354.5 |
| 1-53 | 3-Cl-2-Me-Ph | Me | H | $^1$H NMR(200 MHz, CDCl$_3$): δ 7.65(br, 1 H), 7.20-7.11(m, 2 H), 6.91(s, 1 H), 6.71(s, 1 H), 6.25(d, 1 H, J = 9.8 Hz), 5.62(d, 1 H, J = 9.8 Hz), 2.27(s, 3 H), 2.18(d, 3 H), 1.42(s, 6 H) |
| 1-54 | 4-NO$_2$-Ph | Me | H | m/z 369.4 |
| 1-55 | 3-trifluoro | Me | H | m/z 392.4 |
| 1-56 | phenethyl | Me | H | m/z 352.5 |
| 1-57 | 4-MeO-Ph | Me | CH$_2$CH$_3$ | m/z 366.5 |
| 1-58 | 4-Me-Ph | Me | CH$_2$CH$_3$ | m/z 350.5 |
| 1-59 | 4-Cl-Ph | Me | CH$_2$CH$_3$ | m/z 370.9 |
| 1-60 | 4-O$_2$N-Ph | Me | CH$_2$CH$_3$ | m/z 381.4 |
| 1-61 | 4-F-Ph | Me | CH$_2$CH$_3$ | m/z 354.4 |
| 1-62 | 3,4-di-Me-Ph | Me | CH$_2$CH$_3$ | m/z 364.5 |
| 1-63 | phenylpiperazinyl | Me | CH$_2$CH$_3$ | $^1$H NMR(200 MHz, CDCl$_3$): δ 7.31-7.21(m, 2 H), 6.92-6.85(m, 4 H), 6.73(s, 1 H), 6.61(s, 1 H), 6.24(d, 1 H, J = 10.0 Hz), 5.49(d, 1 H, J = 10.0 Hz), 3.98-3.93(m, 4 H), 3.27-3.21(m, 4 H), 2.17(s, 3 H), 1.71-1.57(m, 2 H), 1.51-1.38(m, 2 H), 1.35(s, 3 H), 0.93-0.86(m, 3 H) |
| 1-64 | 4-Cl-Bn | Me | CH$_2$CH$_3$ | m/z 400.9 |
| 1-65 | methyl piperidine-4-carboxylate | Me | CH$_2$CH$_3$ | $^1$H NMR(200 MHz, CDCl$_3$): δ 6.87(br, 1 H), 6.68(s, 1 H), 6.58(s, 1 H), 6.23(d, 1 H, J = 10.2 Hz), 5.48(d, 1 H, J = 10.2 Hz), 4.35(br, 2 H), 3.67(s, 3 H), 3.22(br, 2 H), 2.59-2.49(m, 1 H), 2.14(s, 3 H), 2.02-1.50(br, 6 H), 1.46-1.34(m, 5 H), 0.88(t, 3 H, J = 7.3 Hz) |

TABLE 1g

| No. | R | R' | R'' | Data |
|---|---|---|---|---|
| 1-66 | piperidinyl | Me | CH$_2$CH$_3$ | $^1$H NMR(200 MHz, CDCl$_3$): δ 6.78(br, 1 H), 6.70(s, 1 H), 6.58(s, 1 H), 6.23(d, 1 H, J = 10.0 Hz), 5.49(d, 1 H, J = 10.0 Hz), 3.75-3.73(br, 4 H), 2.15(s, 3 H), 1.69-1.56(br, 6 H), 1.52-1.36(m, 2 H), 1.34(s, 6 H), 0.89(t, 3 H, J = 7.1 Hz) |
| 1-67 | N(Me)NH$_2$ | Me | CH$_2$CH$_3$ | $^1$H NMR(200 MHz, CDCl$_3$): δ 9.08(br, 1 H), 7.00(s, 1 H), 6.61(s, 1 H), 6.28(d, 1 H, J = 9.8 Hz), 5.47(d, 1 H, J = 9.8 Hz), 3.71(s, 3 H), 2.17(s, 3 H), 1.74-1.57(m, 2 H), 1.51-1.38(m, 2 H), 1.35(s, 3 H), 0.89(t, 3 H, J = 7.1 Hz) |
| 1-68 | 4-MeO-Ph | H | CH$_2$Ph | m/z 414.5 |
| 1-69 | 4-Me-Ph | H | CH$_2$Ph | m/z 398.5 |
| 1-70 | 4-Cl-Ph | H | CH$_2$Ph | m/z 418.9 |
| 1-71 | 4-O$_2$N-Ph | H | CH$_2$Ph | m/z 429.5 |
| 1-72 | 4-F-Me-Ph | H | CH$_2$Ph | m/z 402.5 |
| 1-73 | 3,4-di-Me-Ph | H | CH$_2$Ph | m/z 412.5 |
| 1-74 | 4-MeO-Ph | Me | CH$_2$Ph | m/z 428.5 |
| 1-75 | 4-Me-Ph | Me | CH$_2$Ph | m/z 412.5 |
| 1-76 | 4-Cl-Ph | Me | CH$_2$Ph | m/z 432.9 |
| 1-77 | 4-O$_2$N-Ph | Me | CH$_2$Ph | m/z 443.5 |
| 1-78 | 4-F-Me-Ph | Me | CH$_2$Ph | m/z 416.5 |
| 1-79 | 3,4-di-Me-Ph | Me | CH$_2$Ph | m/z 426.6 |

Example 2

Synthesis of Guanidine-Based Benzopyran Derivative Formula 1b

Example 2-1

Synthesis of N-(2,2'-dimethyl-2-H-chromen-6-yl)-N'-(4-nitrophenyl)-N''-phenyl-guanidine

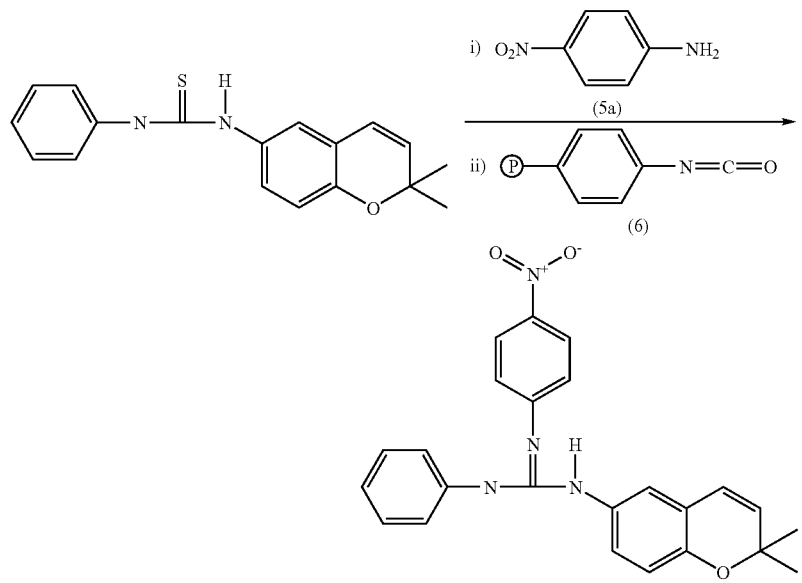

A thiourea compound (50 mg, 0.16 mmol, 1 eq) was added to chloroform (CHCl₃, 5 mL) and stirred at room temperature for 10 min. 1,3-Diisopropylcarbodiimide (DIC; 0.029 mL, 0.19 mmol, 1.2 eq) and diisopropylethylamine (DIPEA; 0.033 mL, 0.19 mmol, 1.2 eq) were added thereto and stirred at 50° C. for 10 min. Subsequently, 4-nitroaniline of Formula (5a) (44 mg, 0.32 mmol) was added thereto and stirred for 15 hrs. After the reaction was completed, the resulting mixture was cooled down to room temperature, polystyrene isocyanate of Formula (6) (2.90 mmol/g, 0.35 g, 1 mmol) was added thereto, and stirred for 30 min. After the reaction mixture was filtered, the filtrate thus obtained was repeatedly washed with chloroform (CHCl₃) and collected. The resulting reactant was concentrated under reduced pressure and the residue thus obtained was purified with a silica gel column chromatography using a mixed solvent of hexane/ethylacetate (3/1, v/v), to obtain the title compound (35 mg) with a yield of 53%.

Example 2-2

Synthesis of N-(2,2'-dimethyl-2H-chromen-6-yl)-N'-(4-nitrophenyl)-N''-4-tolyl-guanidine

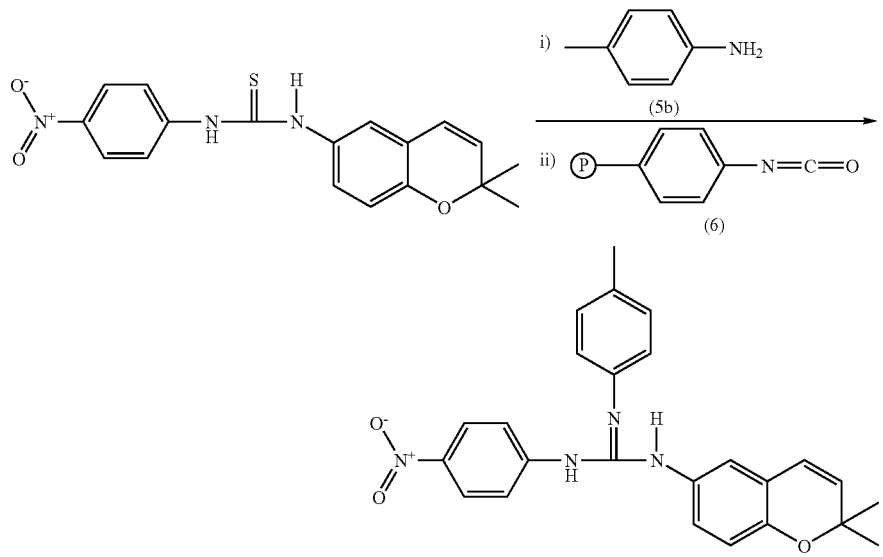

A thiourea compound (69 mg, 0.16 mmol, 1 eq) was added to chloroform (CHCl$_3$, 5 mL) and stirred at room temperature for 10 min. 1,3-Diisopropylcarbodiimide (DIC; 0.029 mL, 0.19 mmol, 1.2 eq) and diisopropylethylamine (DIPEA; 0.033 mL, 0.19 mmol, 1.2 eq) were added thereto and stirred at 50° C. for 10 min. Subsequently, 4-methylaniline of Formula (5b) (0.035 mL, 0.32 mmol) was added thereto and stirred for 15 hrs. After the reaction was completed, the resulting mixture was cooled down to room temperature, polystyrene isocyanate of Formula (6) (2.90 mmol/g, 0.35 g, 1 mmol) was added thereto, and stirred for 30 min. After the reaction mixture was filtered, the filtrate thus obtained was repeatedly washed with chloroform (CHCl$_3$) and collected. The resulting reactant was concentrated under reduced pressure and the residue thus obtained was purified with a silica gel column chromatography using a mixed solvent of hexane/ethylacetate (3/1, v/v), to obtain the title compound (34 mg) with a yield of 49%.

A thiourea compound (64 mg, 0.16 mmol, 1 eq) was added to chloroform (CHCl$_3$, 5 mL) and stirred at room temperature for 10 min. 1,3-Diisopropylcarbodiimide (DIC; 0.029 mL, 0.19 mmol, 1.2 eq) and diisopropylethylamine (DIPEA; 0.033 mL, 0.19 mmol, 1.2 eq) were added thereto and stirred at 50° C. for 10 min. Subsequently, 4-fluoroaniline of Formula (5c) (0.030 mL, 0.32 mmol) was added thereto and stirred for 15 hrs. After the reaction was completed, the resulting mixture was cooled down to room temperature, polystyrene isocyanate of Formula (6) (2.90 mmol/g, 0.35 g, 1 mmol) was added thereto, and stirred for 30 min. After the reaction mixture was filtered, the filtrate thus obtained was repeatedly washed with chloroform (CHCl$_3$) and collected. The resulting reactant was concentrated under reduced pressure and the residue thus obtained was purified with a silica gel column chromatography using a mixed solvent of hexane/ethylacetate (3/1, v/v), to obtain the title compound (44 mg) with a yield of 58%.

Example 2-3

Synthesis of N-(2,2'-dimethyl-2H-chromen-6-yl)-N'-(4-fluorophenyl)-N"-(4-nitrophenyl)-guanidine Example 2-4

Synthesis of N-(2,2'-dimethyl-2H-chromen-6-yl)-N'-(4-methoxyphenyl)-N"-(4-nitrophenyl)-guanidine

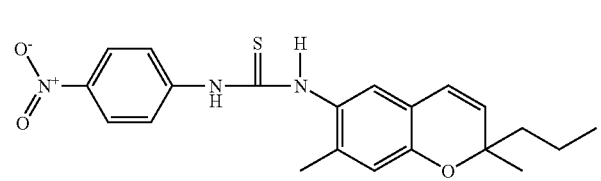

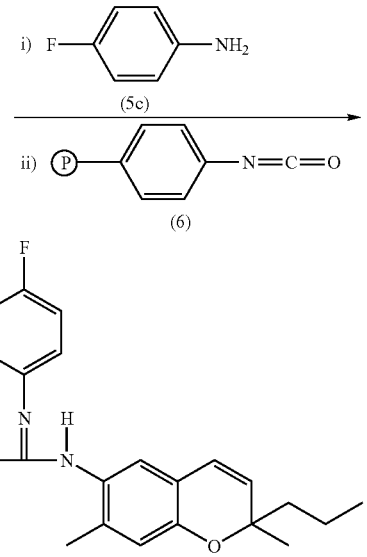

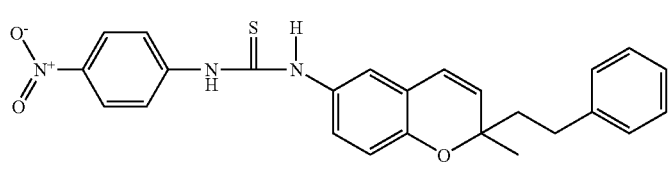

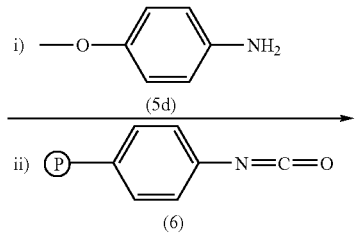

-continued

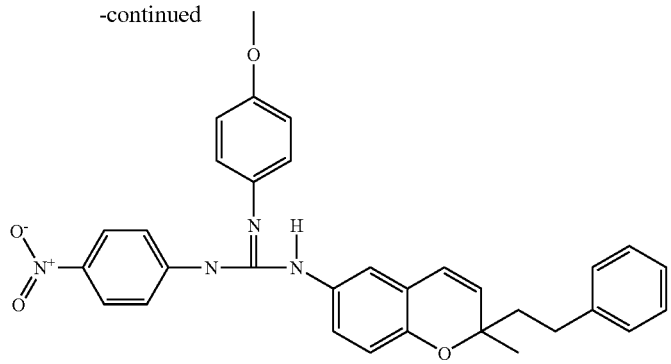

15

A thiourea compound (71 mg, 0.16 mmol, 1 eq) was added to chloroform (CHCl₃, 5 mL) and stirred at room temperature for 10 min. 1,3-Diisopropylcarbodiimide (DIC; 0.029 mL, 0.19 mmol, 1.2 eq) and diisopropylethylamine (DIPEA; 0.033 mL, 0.19 mmol, 1.2 eq) were added thereto and stirred at 50° C. for 10 min. Subsequently, 4-methoxyaniline of Formula (5d) (39 mg, 0.32 mmol) was added thereto and stirred for 15 hrs. After the reaction was completed, the resulting mixture was cooled down to room temperature, polystyrene isocyanate of Formula (6) (2.90 mmol/g, 0.35 g, 1 mmol) was added thereto, and stirred for 30 min. After the reaction mixture was filtered, the filtrate thus obtained was repeatedly washed with chloroform (CHCl₃) and collected. The resulting reactant was concentrated under reduced pressure and the residue thus obtained was purified with a silica gel column chromatography using a mixed solvent of hexane/ethylacetate (3/1, v/v), to obtain the title compound (37 mg) with a yield of 43%.

The guanidine-based benzopyran derivative of Formula (1b), as a target compound of the present invention was synthesized according to the same method as described in Example 2, and the results are shown in the following Tables 2a to 2e.

TABLE 2a

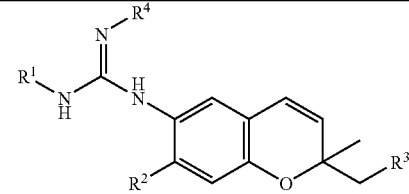

(1b)

| Com. No | $R^1$ | $R^2$ | $R^3$ | $R^4$ | Structural data |
|---|---|---|---|---|---|
| 2-1 | Ph | H | H | Ph | m/z 369.48 |
| 2-2 | Ph | H | H | 4-Me-Ph- | m/z 383.49 |
| 2-3 | Ph | H | H | 4-F-Ph- | ¹H NMR(300 MHz, CDCl₃) δ 7.36-7.31(m, 5 H), 7.01(m, 2 H), 6.86(t, 2 H, J = 8.7 Hz), 6.65(d, 1 H), 6.64-6.61(m, 2 H), 6.32(d, 1 H), 5.72(d, 1 H), 1.43(s, 6 H); m/z 387.46 |
| 2-4 | Ph | H | H | 4-Cl-Ph- | m/z 403.92 |
| 2-5 | Ph | H | H | 4-MeO-Ph- | ¹H NMR(300 MHz, CDCl₃) δ 7.29-7.11(m, 7 H), 6.95(d, 2 H, J = 8.1 Hz), 6.86-6.81(m, 2 H), 6.67(d, 2 H, J = 7.2 Hz), 6.25(d, 1 H), 5.62(d, 1 H, J = 9.9 Hz), 3.75(s, 3 H), 1.38(s, 6 H); m/z 399.47 |
| 2-6 | Ph | H | H | 4-NO₂-Ph- | ¹H NMR(300 MHz, CDCl₃) δ 8.08(d, 2 H, J = 8.9 Hz), 7.34-7.16(m, 7 H), 6.90(dd, 1 H, J = 8.6 Hz, J = 2.5 Hz), 6.82(d, 1 H, J = 2.5 Hz), 6.71(d, 1 H, J = 8.6 Hz), 6.23(d, 1 H, J = 9.8 Hz), 5.65(d, 1 H, J = 9.8 Hz), 1.41(s, 6 H); m/z 414.46 |
| 2-7 | Ph | H | H | Bn— | m/z 383.47 |
| 2-8 | 4-O₂N-Ph | H | H | 4-Me-Ph- | ¹H NMR(300 MHz, CDCl₃) δ 8.02(d, 2 H, J = 8.9 Hz), 7.21(d, 2 H, J = 8.9 Hz), 7.08(s, 4 H), 6.1 (dd, 1 H, J = 8.4 Hz, J = 2.4 Hz), 6.84(d, 1 H, J = 2.4 Hz), 6.66(d, 1 H, J = 8.4 Hz), 6.21(d, 1 H, J = 9.9 Hz), 5.63(d, 1 H, J = 9.9 Hz), 2.27(s, 3 H), 1.38(s, 6 H); m/z 428.50 |
| 2-9 | 4-O₂N-Ph | H | H | 3,5-Me-Ph- | ¹H NMR(300 MHz, CDCl₃) δ 8.05(d, 2 H, J = 8.97 Hz), 7.20(d, 2 H, J = 8.97 Hz), 6.89 (dd, 1 H, J = 8.46 Hz, J = 2.49 Hz), 6.82(d, 1 H, J = 2.49 Hz), 6.77(s, 3 H), 6.69(d, 1 H, J = 8.46 Hz), 6.22(d, 1 H, J = 9.83 Hz), 5.64(d, 1 H, J = 9.83 Hz), 2.24(s, 6 H), 1.39(s, 6 H); m/z 442.55 |

TABLE 2b

| | | | | | |
|---|---|---|---|---|---|
| 2-10 | 4-O$_2$N-Ph | H | H | 4-F-Ph- | $^1$H NMR(300 MHz, CDCl$_3$) δ 8.10(d, 2H, J = 9.0 Hz), 7.26(d, 2H, J = 9.0 Hz), 7.17(m, 2H), 6.99(m, 2H), 6.91 (dd, 1H, J = 8.4 Hz, J = 2.4 Hz), 6.81(d, 1H, J = 2.4 Hz), 6.73(d, 1H, J = 8.4 Hz), 6.24(d, 1H, J = 9.9 Hz), 5.66(d, 1H, J = 9.9 Hz), 1.42(s, 6H); m/z 432.47 |
| 2-11 | 4-O$_2$N-Ph | H | H | 4-Cl-Ph- | $^1$H NMR(300 MHz, CDCl$_3$) δ 8.12(d, 2H, J = 7.6 Hz), 7.29-7.14(m, 4H), 7.10(d, 2H, J = 8.7 Hz), 6.90(d, 1H, J = 2.6 Hz), 6.79-6.71(m, 2H), 6.23(d, 1H, J = 9.8 Hz), 5.66(d, 1H, J = 9.8 Hz), 1.40(s, 6H); m/z 448.93 |
| 2-12 | 4-O$_2$N-Ph | H | H | 4-MeO-Ph- | $^1$H NMR(300 MHz, CDCl$_3$) δ 8.11(d, 2H, J = 8.9 Hz), 7.24(d, 2H, J = 8.9 Hz), 7.14(d, 2H, J = 8.8 Hz), 6.93(dd, 1H, J = 8.5 Hz, J = 2.3 Hz), 6.86(m, 3H), 6.73(d, 1H, J = 8.5 Hz), 6.25(d, 1H, J = 9.8 Hz), 5.64(d, 1H, J = 9.8 Hz), 3.78(s, 3H), 1.42(s, 6H); m/z 444.50 |
| 2-13 | 4-O$_2$N-Ph | H | H | 2-MeO-Ph- | m/z 444.51 |
| 2-14 | 4-O$_2$N-Ph | H | H | iso-valine (methyl ester)- | m/z 452.54 |
| 2-15 | 4-O$_2$N-Ph | H | H | Bn- | m/z 428.48 |
| 2-16 | 4-O$_2$N-Ph | H | H | 4-F-Bn- | $^1$H NMR(300 MHz, CDCl$_3$) δ 8.14(d, 2H, J = 8.99 Hz), 7.27(m, 2H), 7.12(d, 2H, J = 8.99 Hz), 7.03(m, 2H), 6.85(dd, 1H, J = 8.49 Hz, J = 2.60 Hz), 6.74(d, 1H, J = 2.60 Hz), 6.70(d, 1H, J = 8.49 Hz), 6.20(d, 1H, J = 9.85 Hz), 5.65(d, 1H, J = 9.85 Hz), 4.45(s, 2H), 1.41(s, 6H); m/z Z 446.49 |
| 2-17 | 4-O$_2$N-Ph | H | H | 4-Cl-Bn- | m/z 462.95 |
| 2-18 | 4-O$_2$N-Ph | H | H | 4-NO$_2$-Ph- | $^1$H NMR(300 MHz, CDCl$_3$) δ 8.14(d, 2H, J = 9.32 Hz), 8.12(d, 2H, J = 8.49 Hz), 6.96(d, 2H, J = 8.49 Hz), 6.82(d, 2H, J = 9.32 Hz), 6.70(m, 2H), 6.62(s, 1H), 6.22(d, 1H, J = 9.81 Hz), 5.66(d, 1H, J = 9.81 Hz), 3.55(t, 4H, J = 4.11 Hz), 3.45(br-s, 4H), 1.41(s, 6H); m/z 528.55 |
| 2-19 | 4-O$_2$N-Ph | H | H | Ph-piperazine- | $^1$H NMR(300 MHz, CDCl$_3$) δ 8.10(d, 2H, J = 8.7 Hz), 7.30(d, 2H, J = 8.7 Hz), 6.92(m, 5H), 6.75(br-s, 1H), 6.68(d, 1H, J = 8.1 Hz), 6.63(br-s, 1H), 6.22(d, 1H, J = 9.9 Hz), 5.64(d, 1H, J = 9.9 Hz), 3.54(t, 4H, J = 5.0 Hz), 3.18(br-s, 4H), 1.41(s, 6H); m/z 483.57 |

TABLE 2c

| | | | | | |
|---|---|---|---|---|---|
| 2-20 | 4-O$_2$N-Ph | H | H | 2-MeO-Ph-piperazine- | $^1$H NMR(300 MHz, CDCl$_3$) δ 8.10(d, 2H, J = 8.7 Hz), 7.06-6.92(m, 4H), 6.88(d, 2H, J = 8.7 Hz), 6.74(br-s, 1H), 6.68(d, 1H, J = 8.1 Hz), 6.62(br-s, 1H), 6.22(d, 1H, J = 9.9 Hz), 5.64(d, 1H, J = 9.9 Hz), 3.86(s, 3H), 3.57(t, 4H, J = 4.8 Hz), 3.06(br-s, 4H), 1.41(s, 6H); m/z 513.63 |
| 2-21 | 4-O$_2$N-Ph | H | H | 3-MeO-Ph-piperazine- | $^1$H NMR(300 MHz, CDCl$_3$) δ 8.08(d, 2H, J = 8.40 Hz), 7.18(m, 1H), 6.93(d, 2H, J = 8.4 Hz), 6.75(br-s, 1H), 6.67(d, 1H, J = 8.40 Hz), 6.63(br-s, 1H), 6.53(d, 1H, J = 9.03 Hz), 6.45(m, 2H), 6.21 (d, 1H, J = 9.78 Hz), 5.64(d, 1H, J = 9.78 Hz), 3.79(s, 3H), 3.52(t, 4H, J = 4.91 Hz), 3.17(br-s, 4H), 1.41(s, 6H); m/z 513.64 |
| 2-22 | 4-O$_2$N-Ph | H | H | 4-F-Ph-piperazine- | $^1$H NMR(300 MHz, CDCl$_3$) δ 8.11(d, 2H, J = 9.0 Hz), 7.03-6.95(m, 3H), 6.91-6.85(m, 2H), 6.74(br-s, 1H), 6.69(d, 1H, J = 8.1 Hz), 6.62(br-s, 1H), 6.22(d, 1H, J = 9.9 Hz), 5.65(d, 1H, J = 9.9 Hz), 3.53(t, 4H, J = 5.0 Hz), 3.09(br-s, 4H), 1.41(s, 6H); m/z 501.58 |
| 2-23 | 4-O$_2$N-Ph | H | H | 4-Cl-Ph-piperazine- | $^1$H NMR(300 MHz, CDCl$_3$) δ 8. 10(d, 2H, J = 8.7 Hz), 7.22(d, 2H, J = 7.5 Hz), 6.94(d, 2H, J = 8.7 Hz), 6.83(d, 2H, J = 7.5 Hz), 6.75(br-s, 1H), 6.68(d, 1H, J = 8.4 Hz), 6.62(br-s, 1H), 6.21 (d, 1H, J = 9.9 Hz), 5.64(d, 1H, J = 9.9 Hz), 3.52(t, 4H, J = 5.3 Hz), 3.13(br-s, 4H), 1.41(s, 6H); m/z 518.03 |
| 2-24 | 4-O$_2$N-Ph | H | H | 4-Me-Ph-piperazine- | m/z 497.61 |
| 2-25 | 4-O$_2$N-Ph | H | H | 3,4-dioxo-Bn- | $^1$H NMR(300 MHz, CDCl$_3$) δ 8.14(d, 2H, J = 8.9 Hz), 7.16(d, 2H, J = 8.9 Hz), 6.87(dd, 1H, J = 8.5 Hz, J = 2.5 Hz), 6.81-6.76(m, 4H), 6.70(d, 1H, J = 8.5 Hz), 6.21 (d, 1H, J = 9.8 Hz), 5.96(s, 2H), 5.64(d, 1H, J = 9.8 Hz), 4.42(s, 2H), 1.40(s, 6H); m/z 472.51 |

TABLE 2c-continued

| | | | | | |
|---|---|---|---|---|---|
| 2-26 | 4-O$_2$N-Ph | CH$_3$ | —CH$_2$CH$_3$ | Ph- | $^1$H NMR(300 MHz, CDCl$_3$) δ 8.13(d, 2H), 7.33-7.23(m, 7H), 7.10(t, 1H), 6.82(s, 1H), 6.65(s, 1H), 6.27(d, 1H), 5.56(d, 1H), 5.64(d, 1H, J = 9.8 Hz), 2.20(s, 3H), 1.62(m, 2H), 1.46(m, 2H), 1.37(s, 3H), 0.92(t, 3H); m/z 456.54 |

TABLE 2d

| | | | | | |
|---|---|---|---|---|---|
| 2-27 | 4-O$_2$N-Ph | CH$_3$ | —CH$_2$CH$_3$ | 4-Me-Ph- | $^1$H NMR(300 MHz, CDCl$_3$) δ 8.06(d, 2H), 7.22(d, 2H), 7.05(m, 4H), 6.82(s, 1H), 6.59(s, 1H), 6.25(d, 1H), 5.54(d, 1H), 2.28(s, 3H), 2.04(s, 3H), 1.64(m, 2H), 1.58(m, 2H), 1.37(s, 3H), 0.90(t, 3H); m/z 470.58 |
| 2-28 | 4-O$_2$N-Ph | CH$_3$ | —CH$_2$Cn3 | 4-MeO-Ph- | $^1$H NMR(300 MHz, CDCl$_3$) δ 8.10(d, 2H), 7.28(d, 2H), 7.15(d, 2H), 6.86(m, 3H), 6.62(s, 1H), 6.26(d, 1H), 5.55(d, 1H), 3.78(s, 3H), 2.20(s, 3H), 1.66(m, 2H), 1.60(m, 2H), 1.40(s, 3H), 0.91 (t, 3H); m/z 486.56 |
| 2-29 | 4-O$_2$N-Ph | CH$_3$ | —CH$_2$CH$_3$ | 4-F-Ph- | $^1$H NMR(500 MHz, CDCl$_3$) δ 8.10(d, 2H), 7.26(d, 2H), 7.16(m, 2H) 6.80(s, 1H) 6.98(t, 2H), 6.80(s, 1H), 6.61(s, 1H), 6.25(d, 1H), 5.55(d, 1H), 2.20(s, 3H), 1.65(m, 2H), 1.41(m, 2H), 1.35(s, 3H), 0.91 (t, 3H, J = 7.30 Hz); m/z 474.52 |
| 2-30 | 4-O$_2$N-Ph | CH$_3$ | —CH$_2$CH$_3$ | 4-Cl-Ph- | $^1$H NMR(500 MHz, CDCl$_3$) δ 8.15(d, 2H, J = 9.05 Hz), 7.28(d, 2H, J = 9.05 Hz), 7.10(d, 2H, J = 8.70 Hz), 6.80(s, 1H), 6.66(s, 1H), 6.61 (d, 2H, J = 8.70 Hz), 6.27(d, 1H, J = 9.95 Hz), 5.57(d, 1H, J = 9.95 Hz), 2.20(s, 3H), 1.68(m, 2H), 1.60(m, 2H), 1.38(s, 3H), 0.92(t, 3H, J = 7.30 Hz); m/z 490.99 |
| 2-31 | 4-O$_2$N-Ph | CH$_3$ | —CH$_2$CH$_3$ | 4-NO$_2$-Ph- | $^1$H NMR(300 MHz, CDCl$_3$) δ 8.18(d, 4H, J = 9.2 Hz), 7.53(d, 2H, J = 9.2 Hz), 7.40(br-s, 2H), 6.83(s, 1H), 6.67(s, 1H), 6.27(d, 1H, J = 9.9 Hz), 5.59(d, 1H, J = 9.9 Hz), 2.22(s, 3H), 1.62-1.43(m, 4H), 1.38(s, 3H), 0.93(m, 3H); m/z 501.55 |
| 2-32 | 4-O$_2$N-Ph | CH$_3$ | —CH$_2$CH$_3$ | morpholine- | $^1$H NMR(300 MHz, CDCl$_3$) δ 8.09(d, 2H, J = 8.2 Hz), 6.94(d, 2H, J = 8.2 Hz), 6.70(s, 1H), 6.54(s, 1H), 6.25(d, 1H, J = 10.1 Hz), 5.55(d, 1H, J = 10.1 Hz), 3.64(m, 4H), 3.32(m, 4H), 2.04(s, 3H), 1.68-1.57(m, 2H), 1.47-1.43(m, 2H), 1.34(s, 3H), 0.91 (t, 3H, J = 7.2 Hz); m/z 450.55 |
| 2-33 | 4-O$_2$N-Ph | CH$_3$ | —CH$_2$CH$_3$ | (CH$_2$CH$_3$)$_2$— | $^1$H NMR(300 MHz, CDCl$_3$) δ 8.08(d, 2H, J = 9.0 Hz), 7.05(d, 2H, J = 9.0 Hz), 6.68(s, 1H), 6.55(s, 1H), 6.23(d, 1H, J = 9.9 Hz), 5.54(d, 1H, J = 9.9 Hz), 3.29(q, 4H, J = 7.2 Hz), 2.16(s, 3H), 1.64-1.57(m, 4H), 1.33(s, 3H), 1.17(t, 3H, J = 7.2 Hz), 0.90(t, 6H, J = 7.2 Hz); m/z 436.54 |
| 2-34 | 4-O$_2$N-Ph | H | —CH$_2$Ph | Ph- | m/z 504.59 |
| 2-35 | 4-O$_2$N-Ph | H | —CH$_2$Ph | 4-Me-Ph- | m/z 518.63 |
| 2-36 | 4-O$_2$N-Ph | H | —CH$_2$Ph | 4-MeO-Ph- | m/z 534.62 |
| 2-37 | 4-O$_2$N-Ph | H | —CH$_2$Ph | 4-F-Ph- | m/z 522.59 |

TABLE 2e

| | | | | | |
|---|---|---|---|---|---|
| 2-38 | 4-O$_2$N-Ph | H | —CH$_2$Ph | 4-Cl-Ph- | m/z 539.02 |
| 2-39 | 4-O$_2$N-Ph | H | —CH$_2$Ph | 4-NO$_2$-Ph- | m/z 549.56 |
| 2-40 | 4-O$_2$N-Ph | CH$_3$ | —CH$_2$Ph | Ph- | m/z 518.63 |
| 2-41 | 4-O$_2$N-Ph | CH$_3$ | —CH$_2$Ph | 4-Me-Ph- | m/z 532.65 |
| 2-42 | 4-O$_2$N-Ph | CH$_3$ | —CH$_2$Ph | 4-MeO-Ph- | m/z 548.65 |
| 2-43 | 4-O$_2$N-Ph | CH$_3$ | —CH$_2$Ph | 4-F-Ph- | m/z 536.64 |
| 2-44 | 4-O$_2$N-Ph | CH$_3$ | —CH$_2$Ph | 4-Cl-Ph- | m/z 553.07 |
| 2-45 | 4-O$_2$N-Ph | CH$_3$ | —CH$_2$Ph | 4-NO$_2$-Ph- | m/z 563.63 |
| 2-46 | 4-O$_2$N-Ph | CH$_3$ | —CH$_2$Ph | Ph-piperazine- | m/z 587.74 |
| 2-47 | 4-O$_2$N-Ph | CH$_3$ | —CH$_2$Ph | 2-MeO-Ph-piperazine- | m/z 617.76 |
| 2-48 | 4-O$_2$N-Ph | CH$_3$ | —CH$_2$Ph | 3-MeO-Ph-piperazine- | m/z 617.76 |
| 2-49 | 4-O$_2$N-Ph | CH$_3$ | —CH$_2$Ph | 4-F-Ph-piperazine- | m/z 605.72 |
| 2-50 | 4-O$_2$N-Ph | CH$_3$ | —CH$_2$Ph | 4-Cl-Ph-piperazine- | m/z Z 622.17 |
| 2-51 | 4-O$_2$N-Ph | CH$_3$ | —CH$_2$Ph | 4-Me-Ph-piperazine- | m/z 601.76 |
| 2-52 | 4-O$_2$N-Ph | CH$_3$ | Ph | Ph- | m/z 490.5 |

The following Examples are given for the purpose of illustration only of several methods for preparing a formulation comprising the inventive compound as an active ingredient, but they should be construed as limiting the scope of the present invention.

Formulation 1: Tablet (Direct Pressurization)

After sieving 5.0 mg of the active ingredient, it was mixed with 14.1 mg of lactose, 0.8 mg of crospovidone USNF and 0.1 mg of magnesium stearate, and the mixture was subjected to direct pressurization to be formulated into a tablet.

Formulation 2: Tablet (Wet Granulation)

After sieving 5.0 mg of the active ingredient, it was mixed with 16.0 mg of lactose and 4.0 mg of starch. After 0.3 mg of Polysorbate 80 was dissolved in pure water, the proper amount of the resulting solution was added to the mixture and subjected to granulation. After drying, the granules were sieved and mixed with 2.7 mg of colloidal silicon dioxide and 2.0 mg of magnesium stearate. The resulting granules were subjected to pressurization to be formulated into a tablet.

Formulation 3: Powder and Capsule

After sieving 5.0 mg of the active ingredient, it was mixed with 14.8 mg of lactose, 10.0 mg of polyvinyl pyrrolidone and 0.2 mg of magnesium stearate. The mixture was filled into a firm No. 5 gelatin capsule using a suitable device.

Formulation 4: Injection

An injection was prepared by mixing 100 mg of the active ingredient, 180 mg of mannitol, 26 mg of $Na_2HPO_4.12H_2O$ and 2974 mg of distilled water.

Experimental Example

Biological Assay

Experimental Example 1

Experiment for Antagonistic Activity on TGF-β Receptor

During the damage of hepatocytes which is a critical step for inducing hepatic fibrosis/liver cirrhosis, TGF-β cytokine produced and secreted by inflammatory cells and Kupffer cells induces the proliferation and differentiation of hepatic stellate cells, which results in the over-production and accumulation of an extracellular matrix such as collagen. Therefore, it is possible to develop a compound capable of inhibiting the proliferation and differentiation of hepatic stellate cells and suppressing a chemotactic mechanism of inflammatory cells through the inhibition of TGF-β function as a therapeutic agent for treating hepatic fibrosis/liver cirrhosis.

Figure 2:
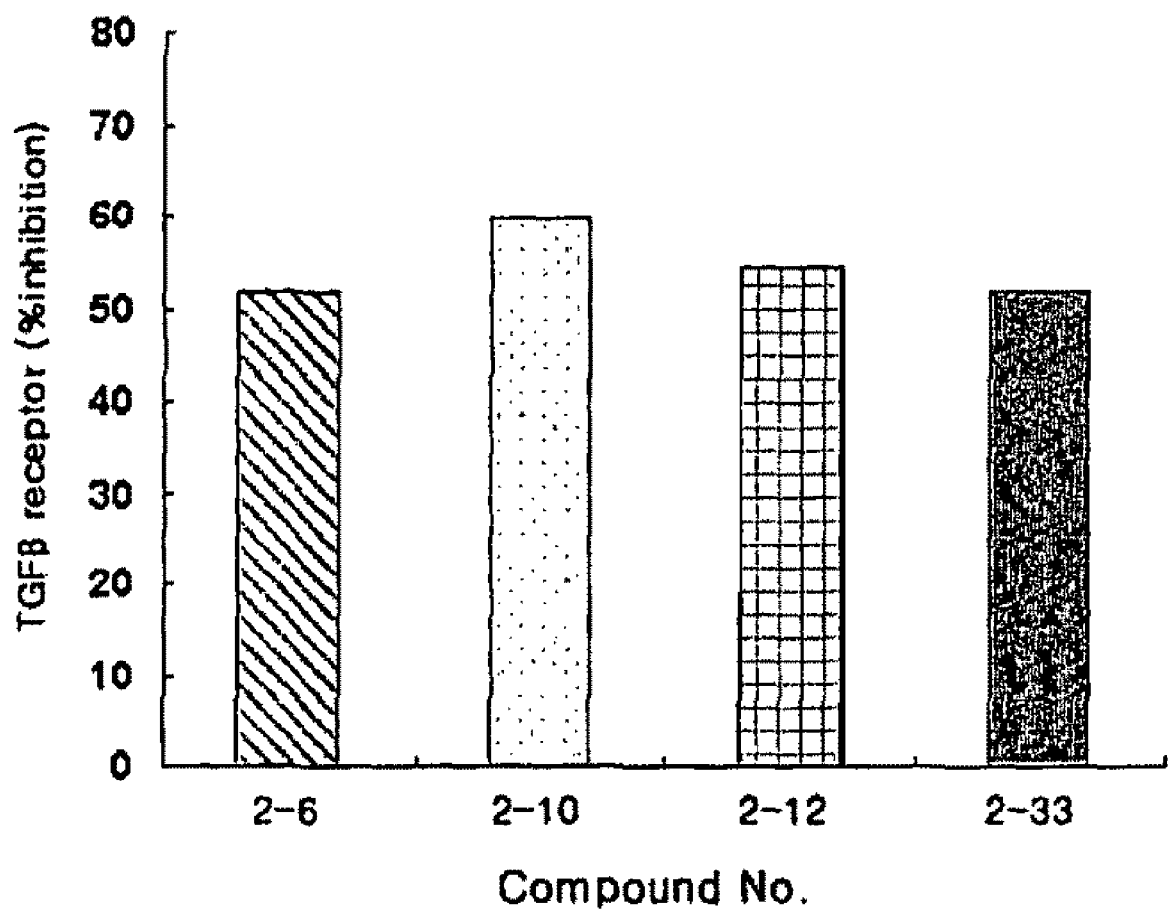
FIG. 2 is a graph showing antagonistic activity on TGF-β receptor of N-(2,7-di substituted-2-methyl-2H-chromen-6-yl)-N,N'-disubstituted guanidine derivative.

The present inventors have carried out an experiment for antagonistic activity on TGF-β receptor to screen a compound capable of blocking a TGF-β-mediated intracellular signal transduction system by competitively inhibiting the binding between TGF-β receptor and its endogenous ligan, TGF-β. TGF-β dissolved in a sodium carbonate solution was added to each well of a well plate and the well plate was incubated at 4° C. overnight to attach TGF-β to the surface of the well. The purified biotin-TGF-β was dissolved in a Tris-HCl buffer, added to the well together with a compound to be experimented, and then, the mixture was kept at room temperature for 1 hour to induce a binding reaction between TGF-β or and biotin-TGF-β. After each well was washed with PBS-0.05% Tween 20 solution (PBST buffer), HRP-conjugated streptavidin was added thereto, and the well plate was kept at room temperature for 1 hour. Each well was washed with the PBST buffer, a TMB solution as a HRP substrate was added thereto, and then, the well plate was kept at room temperature for 20 min to develop a color. The reaction was stopped by adding an equal volume of 1 M phosphoric acid solution. About 5 min after the reaction was stopped, the absorbance of each well was measured at 450 nm of a measurement wavelength and 540 nm of a correction wavelength. As a result, it has been found that the benzopyran derivative in accordance with the present invention shows antagonistic activity on TGF-β receptor. The results of some compounds showing more than 50% of high receptor antagonistic activity are illustrated in FIGS. 1 and 2, respectively. Since it has been hypothesized from the above results that the compounds showing antagonistic activity on TGF-β receptor are also capable of inhibiting the progression of fibrosis in hepatic stellate cells, the following experiments have been conducted.

Experimental Example 2

Experiment on Inhibitory Activity in Collagen Synthesis

Hepatic fibrosis is a procedure that collagen is accumulated by increasing the synthesis of collagen and decreasing the degradation thereof due to the proliferation and activation of hepatic stellate cells. Accordingly, as hepatic fibrosis progresses, the activated hepatic stellate cells stimulate the synthesis of collagen followed by increase in the extracellular secretion of collagen thus synthesized, thereby confirming the inhibitory effect on hepatic fibrosis by observing cytotoxicity and the inhibitory effect on collagen synthesis of hepatic stellate cells.

Figure 3:
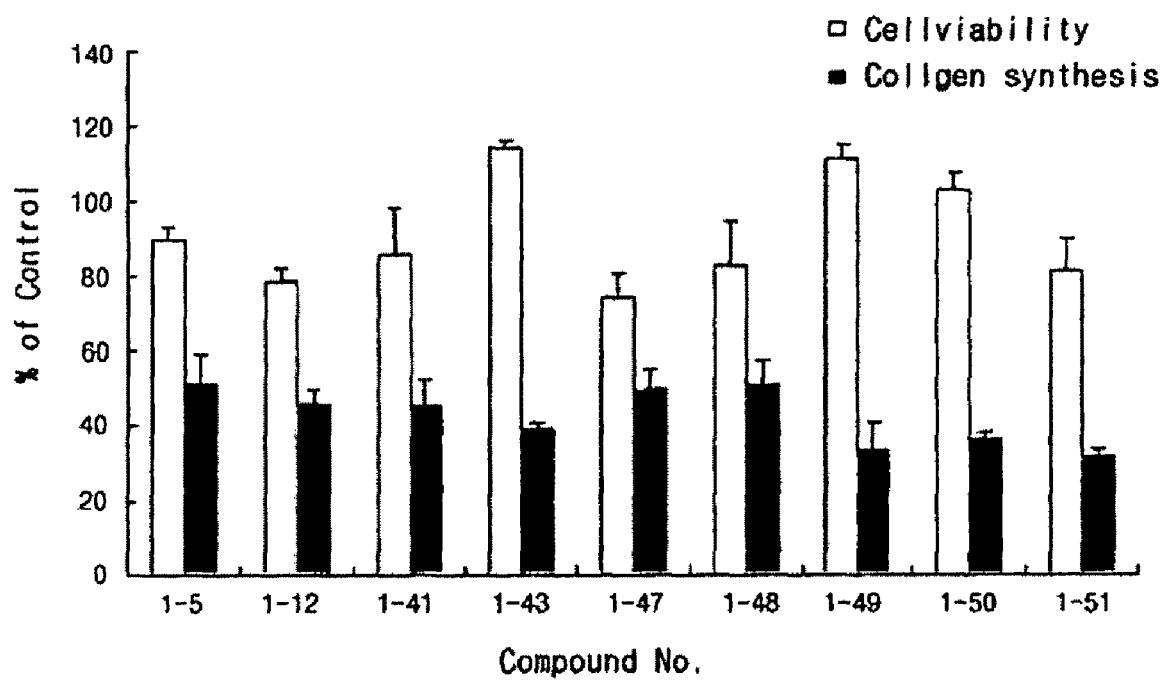
FIG. 3 is a graph showing the effect of N-(2,7-di substituted-2-methyl-2H-chromen-6-yl)thiourea derivative on cytotoxicity and collagen synthesis in LI 90 cells.
Figure 3:
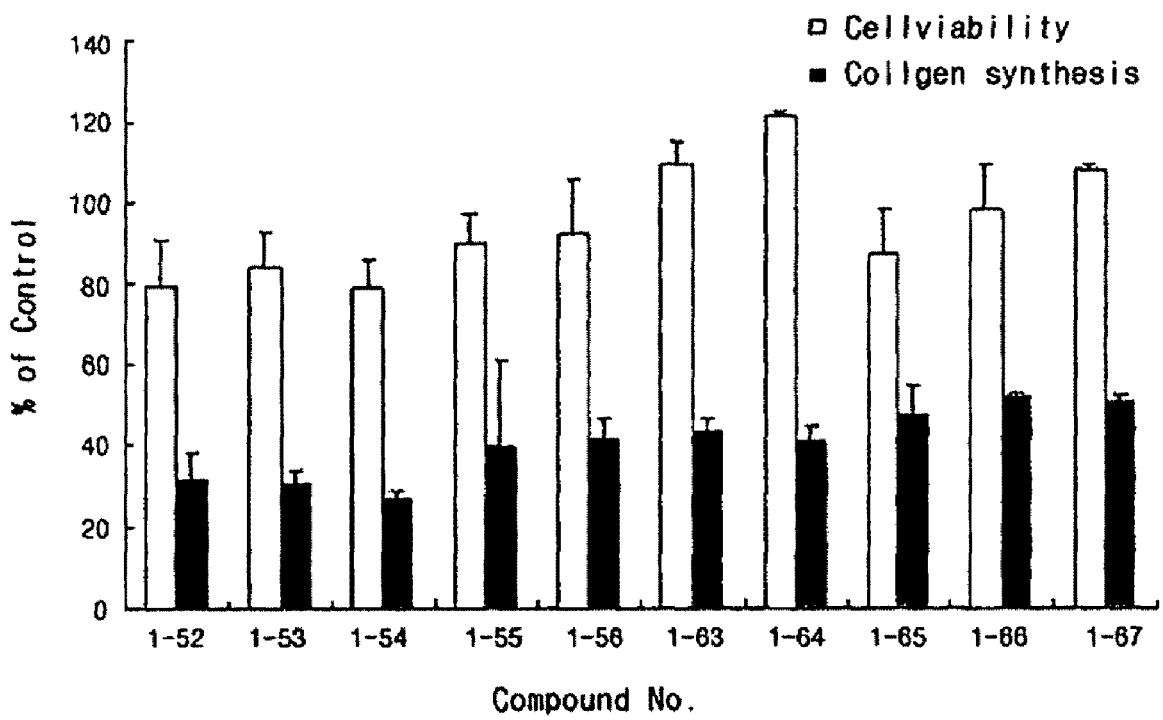
Figure 4:
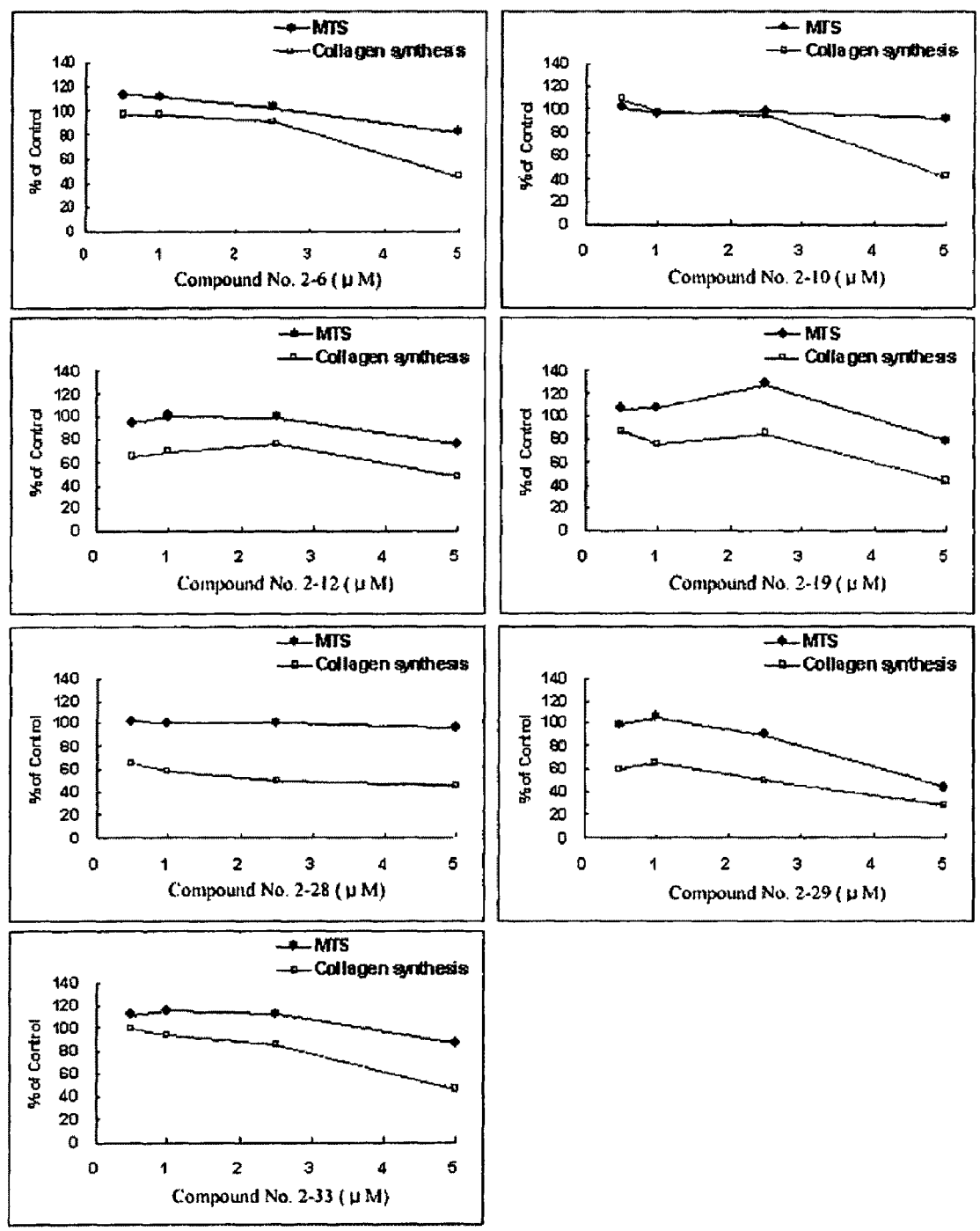
FIG. 4 is a graph showing the effect of N-(2,7-di substituted-2-methyl-2H-chromen-6-yl)-N,N'-disubstituted guanidine derivative on cytotoxicity and collagen synthesis in LI 90 cells.

Human activated hepatic stellate cells, L190 cells were purchased from Japan JCRB (Japanese Collection of Research Bioresources) cell line bank. L190 cell line was cultured at a 96-well plate using a Dulbecco's modified Eagles medium (DMEM) supplemented with 10% fetal bovine serum (FBS) for 24 hrs. After replacing the medium with a fresh one without FBS, a test compound was treated thereto at various concentrations. Forty-eight hrs after the treatment of a test compound, MTS assay was conducted using a CellTiter 96 non-radioactive cell proliferation assay kit (Promega) to measure cytotoxicity. Further, the amount of collagen synthesized within the culture solution was measured by a ELISA method using an anti-rabbit human collagen antibody (ABcam, England), and the results are shown in FIGS. 3 and 4, respectively. Most of the benzopyran derivative compounds of the present invention showing antagonistic activity on TGF-β receptor inhibited the proliferation of hepatic stellate cells, and also suppressed more than 50% of the synthesis and degradation of collagen. Accordingly, it has been found that these compounds have the inhibitory effect on hepatic fibrosis by inhibiting the proliferation of hepatic stellate cells that are abnormally proliferated and activated followed by inducing the development of hepatic fibrosis and suppressing the collagen synthesis and secretion from the cells.

Experimental Example 3

Inhibition of Collagen Gene Expression

Figure 5:
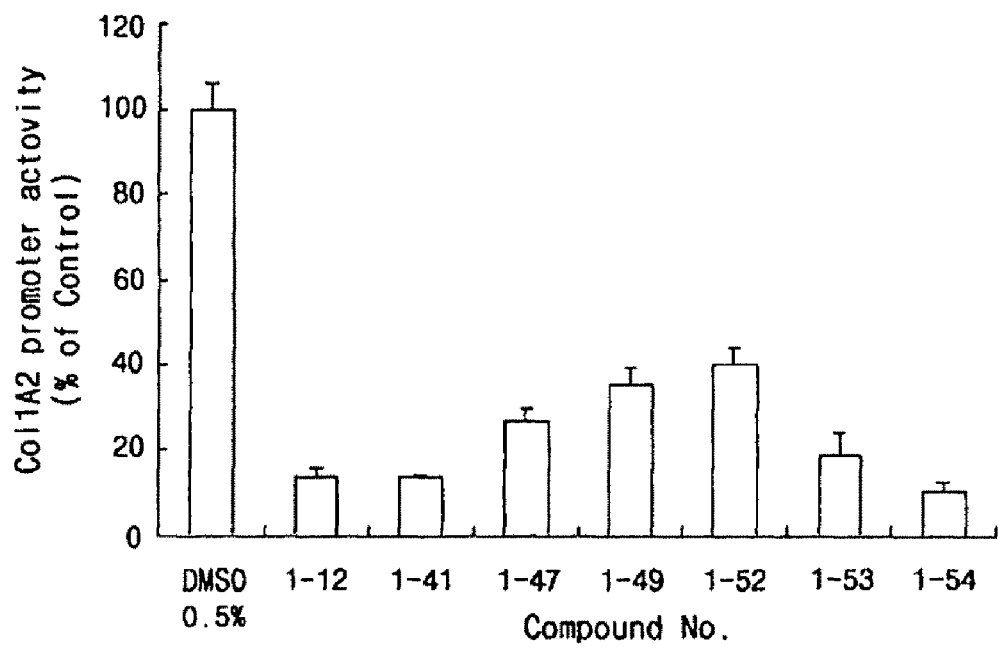
FIG. 5 is a graph showing the effect of N-(2,7-di substituted-2-methyl-2H-chromen-6-yl)thiourea derivative on the expression of a collagen encoding gene in LI 90 cells.
Figure 6:
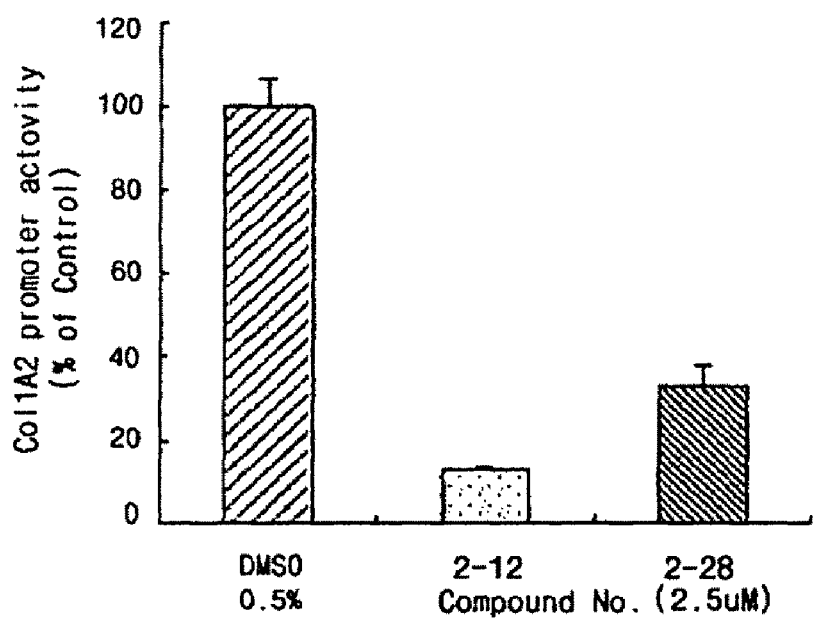
FIG. 6 is a graph showing the effect of N-(2,7-di substituted-2-methyl-2H-chromen-6-yl)-N,N'-disubstituted guanidine derivative on the expression of a collagen encoding gene in LI 90 cells.

Type 1 collagen as a major collagen involved in hepatic fibrosis consists of α1 and α2 chains. Several transcription factors surrounding a collagen gene promoter take part in the expression of a collagen encoding gene, and generally, the amount of collagen expressed is directly proportional to the transcription efficiency of collagen. Therefore, it is capable of measuring a degree of the inhibitory effect on hepatic fibrosis by observing the decrease in the collagen promoter activity. The inhibitory effect on the collagen promoter activity in this Experimental Example was measured as follows.

pCOL1A2-Luc plasmid was prepared by inserting 3.3 kb of a promoter of Type 1 collagen α2 chain (COL1A2) into pGL3 vector comprising a luciferase gene as a receptor gene. In order to correct transfection efficiency, Herpes simplex virus thymidine kinase (HSV-TK) vector comprising a Renilla luciferase gene was prepared. The same L190 cell line as used in Experimental Example 2 was co-transfected with pCOL1A2-Luc plasmid and HSV-TK vector by using a Lipofectamine plus reagent (Life Science, USA). Twenty-four hours after the transfection, the culture medium was replaced with a fresh DMEM without FBS. At this time, a test compound was simultaneously added thereto, the cells were cultured for 24 hrs, and then, subjected to lysis. The luciferase activity was measured by using a dual-luciferase assay kit (Promega). The ratio between the firefly luciferase activity and the Renilla luciferase activity thus obtained was calculated and the degree of activity inhibition was determined from the ratio. The results are shown in FIGS. 5 and 6, respectively. Similar to the results of Experimental Example 2, it has been found that the benzopyran derivative of the present invention inhibits the expression of collagen by experiment results are shown in Table 3 and FIG. 7, respectively.

TABLE 3

| | | | Compound No. | | | |
|---|---|---|---|---|---|---|
| Group | Control | CCl₄ | 1-53 | 1-54 | 1-52 | 1-49 |
| Lesion | Normal | Fibrosis (Grade 2) | Fibrosis (Grade <1) | Fibrosis (Grade <1) | Mild inflammation (Grade 0) | Fibrosis (Grade 1) | reducing more than 60% of Col1A2 promoter activity and suppressing the transcription of a collagen encoding gene.

Experimental Example 4

Prophylactic and Therapeutic Effect on Hepatic Fibrosis/Liver Cirrhosis

When hepatocytes are damaged in the procedure of hepatic fibrosis, Kupffer cells engulf the damaged cells and secrete various cytokines. These cytokines induce the proliferation and activation of hepatic stellate cells (HSCs). The activated hepatic stellate cells synthesize collagen and accumulate it at an extracellular matrix. Finally, hepatic fibrosis is developed by thus continuously accumulated collagen at the extracellular matrix. Carbon tetrachloride (CCl₄) induces liver damage due to the cell membrane destruction and necrosis through a series of actions mediated by an oxidation reaction of free radicals that are generated by the metabolism of cytochrome P450 present within hepatocytes. Accordingly, it is capable of examining the inhibitory effect on hepatic fibrosis by analyzing the decrease in the accumulation of extracellular matrix due to the administration of carbon tetrachloride.

Sprague-dawley male rats (SD, 5-week old) were adapted to experimental environment for 1 week and the rats having about 225 g of an average body weight were used in the following experiment. All the rats in each group (n=12) were abdominally administered with olive oil containing 10% CCl₄ at a concentration of 0.1 mL/kg at a day's interval (three times/week) for 4 weeks, to stably induce chronic hepatic fibrosis. At this time, the experimental animal's survival rate was maintained at 100%. A test compound was dissolved in 0.5% carboxymethylcellulose (CMC) and orally administered to the animals in each experiment group at a concentration of 10 mg/kg, 50 mg/kg, and 200 mg/kg, respectively. The experiment compound's efficacy was determined by histopathological observation of the liver tissue after necropsying the rats in each experiment group at 2-week (n=6) and 4-week (n=6) and fixing the liver tissue extracted therefrom. The histopathological observation was carried out by observing the liver tissues obtained from the perished rats in the experiment group and necropsied rats in the control group with a naked eye, fixing them with 10% neutral formalin, preparing tissue slices according to a conventional paraffin embedding procedure, carrying out a series of H&E (Hematoxylin & Eosin) staining, Azan staining and Toluidine blue staining, and then, observing them with a microscopy. Each of the liver tissues obtained from the negative control, the positive control induced hepatic fibrosis/liver cirrhosis by oral administration of CCl₄, and the experiment group administered with the inventive compound for 2-4 weeks after the oral administration of CCl₄ was observed with Azan staining to analyze their hepatic fibrosis/liver cirrhosis inhibitory and therapeutic effects on connective tissues, and the representative animal As described above, the novel benxopyran derivatives of the present invention shows antagonistic activity on TGF-β receptor, inhibitory effect on the collagen synthesis and inhibitory effect on liver cirrhosis, and accordingly, they can be effectively used for developing a prophylactic and therapeutic agent for treating liver cirrhosis disease.

What is claimed is:

1. A benzopyran derivative of Formula (1) or a pharmaceutically acceptable salt thereof:

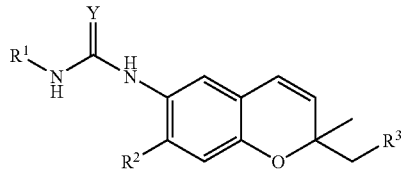

(1)

wherein Y is S or N—R⁴;

R¹ and R⁴ are independently $C_1$-$C_{20}$ alkyl, amine, substituted or unsubstituted phenyl, substituted or unsubstituted benzyl, isovaline(methylester), naphthyl, or phenyl-X-(wherein, X is carbonyl, or $C_1$-$C_6$ alkyl), or R¹ and R⁴ are fused together with the nitrogen atom to which they are attached to form a heterocycle having a 5- to 7-member ring;

R² is hydrogen, or $C_1$-$C_5$ alkyl;

R³ is hydrogen, $C_1$-$C_5$ alkyl, substituted or unsubstituted phenyl, or substituted or unsubstituted benzyl; and wherein the substituted phenyl or the substituted benzyl is phenyl or benzyl substituted with 1 to 4 substituents selected from the group consisting of halogen, nitro, benzyloxy, $C_1$-$C_5$ alkyl, $C_1$-$C_5$ alkoxy, $C_1$-$C_5$ haloalkyl, and $C_1$-$C_5$ alkylsulfanyl.

2. The benzopyran derivative or a pharmaceutically acceptable salt thereof, wherein R¹ and R⁴ are independently $C_1$-$C_{20}$ straight, branched and cyclic alkyl; amine; phenyl; phenyl replaced with 1 to 4 substituents selected from the group consisting of halogen, nitro, benzyloxy, $C_1$-$C_5$ alkyl, $C_1$-$C_5$ alkoxy, $C_1$-$C_5$ haloalkyl, and $C_1$-$C_5$ alkylsulfanyl; benzyl; benzyl replaced with halogen; isovaline(methylester); morphorino; naphthyl; or R¹ and R⁴ are fused together with the nitrogen atom to which they are attached to form piperidine, piperidine replaced with $C_1$-$C_5$ alkoxycarbonyl, piperazine, or piperazine replaced with phenyl;

R² is hydrogen, or $C_1$-$C_5$ alkyl; and

R³ is hydrogen, $C_1$-$C_5$ alkyl, phenyl, or benzyl.

3. A method for preparing the benzopyran derivative of claim 1 which comprises:

synthesizing a thiourea-based benzopyran derivative of Formula (1a) by reacting 6-amino-2,2'-disubstituted-2H-chromen of Formula (2) with an isothiocyanate derivative of Formula (3); and synthesizing a guanidine-based benzopyran derivative of Formula (1b) by reacting the thiourea-based benzopyran derivative of Formula (1a) with an amine derivative of Formula (5):

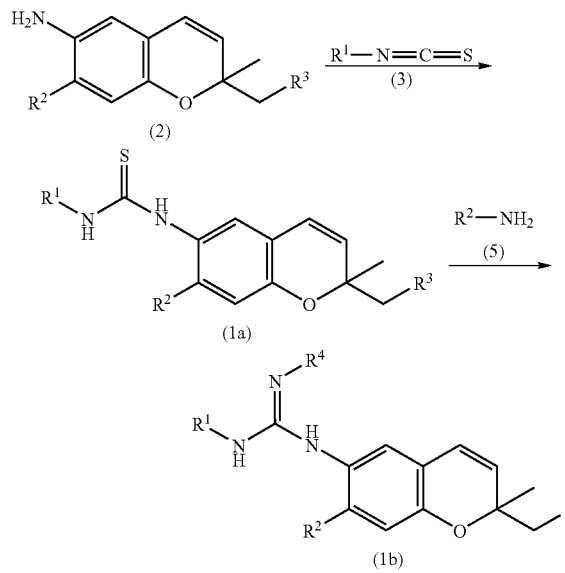

wherein $R^1$, $R^2$, $R^3$, and $R^4$ are the same as defined in claim 1.

4. The method of claim 3, wherein the unreacted isothiocyanate derivative of Formula (3) is removed by filtering with a scavenger resin containing the amine group of Formula (4):

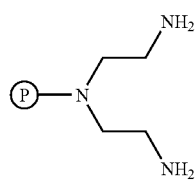

wherein Ⓟ is a solid support in the form of a polymer selected from the group consisting of polystyrene, polystyrene-divinylbenzene, polymethacrylic acid-dimethylacrylamide and polyhydroxy methacrylic acid.

5. The method of claim 3, wherein the unreacted amine derivative of Formula (5) is removed by filtering with a scavenger resin containing the isocyanate group of Formula (6):

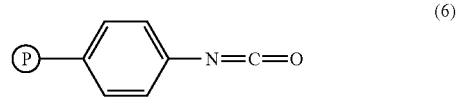

wherein Ⓟ is a solid support in the form of a polymer selected from the group consisting of polystyrene, polystyrene-divinylbenzene, polymethacrylic acid-dimethylacrylamide and polyhydroxy methacrylic acid.

6. A formulation for treating liver disease which comprises the benzopyran derivative of Formula (1) or a pharmaceutically acceptable salt thereof:

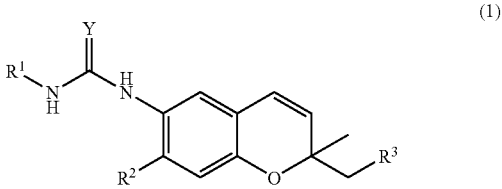

wherein Y, $R^1$, $R^2$, and $R^3$ are the same as defined in claim 1.

7. A formulation for treating fibroplasia disease through antagonistic activity on TGF-β receptor which comprises the benzopyran derivative of Formula (1) or a pharmaceutically acceptable salt thereof:

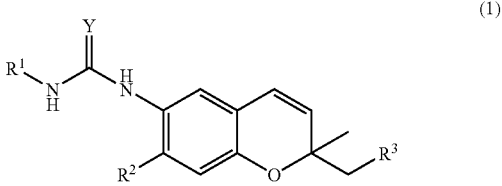

wherein Y, $R^1$, $R^2$, and $R^3$ are the same as defined in claim 1.

8. The formulation of claim 7, wherein the fibroplasia disease includes hepatic fibrosis, liver cirrhosis, pulmonary fibrosis, dermatosclerosis and glomerular fibrosis.

* * * * *